(12) United States Patent
Jung et al.

(10) Patent No.: US 11,653,850 B2
(45) Date of Patent: May 23, 2023

(54) APPARATUS AND METHOD OF MEASURING BIO SIGNAL

(71) Applicant: SAMSUNG ELECTRONICS CO., LTD., Suwon-si (KR)

(72) Inventors: Myounghoon Jung, Bucheon-si (KR); Kak Namkoong, Seoul (KR); Youngjun Koh, Yongin-si (KR); Jungmok Bae, Seoul (KR); Yeolho Lee, Anyang-si (KR); Hyeongseok Jang, Daejeon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 866 days.

(21) Appl. No.: 16/237,310

(22) Filed: Dec. 31, 2018

(65) Prior Publication Data

US 2019/0133487 A1    May 9, 2019

Related U.S. Application Data

(62) Division of application No. 15/266,410, filed on Sep. 15, 2016, now Pat. No. 10,285,620.

(30) Foreign Application Priority Data

Oct. 7, 2015  (KR) .......................... 10-2015-0141040

(51) Int. Cl.
*A61B 5/053*  (2021.01)
*A61B 5/0537*  (2021.01)
(Continued)

(52) U.S. Cl.
CPC .......... *A61B 5/0537* (2013.01); *A61B 5/0205* (2013.01); *A61B 5/026* (2013.01);
(Continued)

(58) Field of Classification Search
CPC . A61B 5/0537; A61B 5/0205; A61B 5/02405; A61B 5/02438; A61B 5/026;
(Continued)

(56) References Cited

U.S. PATENT DOCUMENTS 6,567,692 B1   5/2003  Kohashi et al.
7,423,438 B2   9/2008  Park et al.
(Continued)

FOREIGN PATENT DOCUMENTS

CN    1327375 A    12/2001
CN    102186414 A    9/2011
(Continued)

OTHER PUBLICATIONS

Garcia, et al., "Multilead Measurement Sysem for the Time-Domain-Analysis of Bioimpedance Magnitude", Aug. 2012, IEEE Transactions of Biomedical Engineering, vol. 59, Issue No. 8, pp. 2,273-2,280, XP 011490163.

(Continued)

*Primary Examiner* — Daniel L Cerioni
(74) *Attorney, Agent, or Firm* — Sughrue Mion, PLLC

(57) ABSTRACT

A method of measuring a bio signal using a bio signal measuring apparatus includes: positioning electrodes included as part of the bio signal measuring apparatus to contact a surface of an examinee; switching an impedance measurer included as part of the bio signal measuring apparatus and including a voltmeter and a current source; measuring a first impedance value of the examinee while operating the impedance measurer according to a first mode; switching the impedance measurer to a second mode; measuring a second impedance value of the examinee while operating the impedance measurer according to a second mode; and obtaining bio impedance of the examinee based (Continued)

on the first and second impedance values and an internal impedance of the current source.

7 Claims, 29 Drawing Sheets

(51) Int. Cl.
*A61B 5/00* (2006.01)
*A61B 5/0205* (2006.01)
*A61B 5/024* (2006.01)
*A61B 5/026* (2006.01)
*A61B 5/08* (2006.01)

(52) U.S. Cl.
CPC ...... *A61B 5/02405* (2013.01); *A61B 5/02438* (2013.01); *A61B 5/0809* (2013.01); *A61B 5/4519* (2013.01); *A61B 5/4872* (2013.01); *A61B 5/681* (2013.01); *A61B 5/6826* (2013.01); *A61B 5/7203* (2013.01); *A61B 5/6824* (2013.01); *A61B 2560/0223* (2013.01); *A61B 2560/0468* (2013.01); *A61B 2562/04* (2013.01)

(58) Field of Classification Search
CPC ... A61B 5/0809; A61B 5/4519; A61B 5/4872; A61B 5/681; A61B 5/6826; A61B 5/7203; A61B 5/6824; A61B 2560/0223; A61B 2560/0468; A61B 2562/04
See application file for complete search history.

(56) References Cited

U.S. PATENT DOCUMENTS

| 8,386,028 B2 | 2/2013 | Cha |
| 2004/0181164 A1 | 9/2004 | Smith et al. |
| 2011/0208458 A1 | 8/2011 | Pinter et al. |
| 2013/0053675 A1 | 2/2013 | Kim et al. |
| 2015/0042360 A1 | 2/2015 | Graner et al. |
| 2015/0141856 A1 | 5/2015 | Choi |
| 2016/0174870 A1 | 6/2016 | Lee et al. |

FOREIGN PATENT DOCUMENTS

| EP | 1027861 A1 | 8/2000 |
| EP | 1138258 A1 | 9/2000 |
| JP | 5253446 B2 | 7/2013 |
| KR | 10-0624446 B1 | 9/2006 |
| KR | 10-2008-0102581 A | 11/2008 |
| WO | 2010/044026 A1 | 4/2010 |

OTHER PUBLICATIONS

Communication dated Mar. 10, 2017, issued by the European Patent Office in counterpart European Patent Application No. 16192850.2.
Dai Shengyue, "On the Advantages and Disadvantages of the Two-Wire Method and the Four-Wire Method for Measuring Resistance", Science & Technology Information, No. 34, 2012, pp. 232-233, 9 pages total.
Communication dated Feb. 2, 2021 issued by the State Intellectual Property Office of P.R. China in counterpart Chinese Application No. 201610878731.5.

APPARATUS AND METHOD OF MEASURING BIO SIGNAL

CROSS-REFERENCE TO RELATED APPLICATION

This application is a divisional of U.S. patent application Ser. No. 15/266,410, filed on Sep. 15, 2016, in the U.S. Patent and Trademark Office, and claims priority from Korean Patent Application No. 10-2015-0141040, filed on Oct. 7, 2015, in the Korean Intellectual Property Office, the disclosures of which are incorporated herein in their entireties by reference.

BACKGROUND

1. Field

Methods and apparatuses consistent with the exemplary embodiments disclosed herein relate to apparatuses and methods for measuring a bio signal.

2. Description of the Related Art

A method of positioning an electrode to contact a user's body, measuring bio impedance by using the electrode, and calculating body fat based on the measured bio impedance has been developed. Since a body fat analyzer may accurately measure a degree of body fat accumulation for each portion of a body, the body fat analyzer is used not only in households but also various technical fields.

In the case of measuring body fat by using bio impedance, since measurement is performed by positioning an electrode to directly contact a portion of a user's body, contact impedance due to a contact between the electrode and the user's body influences the measurement of bio impedance.

SUMMARY

Exemplary embodiments provide methods and apparatuses for measuring bio information without an influence of contact impedance.

Exemplary embodiments further provide methods and apparatuses for measuring bio information, that are capable of increasing the accuracy of a measurement value by taking into account internal impedance of a current source.

Technical objects of the exemplary embodiments are not limited to the above technical objects, and other technical objects may be inferred from exemplary embodiments described below.

Additional aspects will be set forth in part in the description which follows and, in part, will be apparent from the description, or may be learned by practice of the presented exemplary embodiments.

According to an aspect of an exemplary embodiment, a method of measuring a bio signal using a bio signal measuring apparatus includes: positioning electrodes included as part of the bio signal measuring apparatus to contact a surface of an examinee; switching an impedance measurer, included as part of the bio signal measuring apparatus and including a voltmeter and a current source, to a first mode, the current source inducing an internal impedance; measuring a first impedance value of the examinee while operating the impedance measurer according to a first mode; switching the impedance measurer to a second mode; measuring a second impedance value of the examinee while operating the impedance measurer according to a second mode; and obtaining bio impedance of the examinee based on the first and second impedance values and the internal impedance of the current source.

The plurality of electrodes may include a first electrode, a second electrode, a third electrode and a fourth electrode, and when the impedance measurer operates according to the first mode, the current source is connected between the first electrode and the fourth electrode, and the voltmeter is connected between the second electrode and the third electrode.

When the impedance measurer operates according to the second mode, the current source is connected between the first electrode and the fourth electrode, and the voltmeter is connected between the second electrode and the third electrode, the first electrode and the second electrode are short-circuited, and the third electrode and the fourth electrode are short-circuited.

The obtaining of the bio impedance of the examinee may include obtaining the bio impedance of the examinee by compensating for an effect of contact impedance between the electrodes and the surface of the examinee in the first and second impedance values considering the internal impedance of the current source.

The obtaining of the bio impedance of the examinee may include: obtaining the bio impedance of the examinee by using Equation 1:

$$Z_m = Z_{4P} \frac{(\beta + Z_i)(\beta + Z_S)}{Z_{4P}(2\beta + Z_i + Z_S) + Z_i Z_S} \quad \text{Equation 1}$$

where $\beta$ is defined by Equation 2, $$\beta = \frac{2}{\frac{1}{Z_{2P}} - \frac{1}{Z_i} - \frac{1}{Z_S}} \quad \text{Equation 2}$$

where $Z_{4P}$=a first impedance value, $Z_{2P}$=a second impedance value, $Z_i$=an input impedance value of the impedance measurer, and $Z_s$=the internal impedance of the current source.

The method may further include changing an effective value of the internal impedance of the current source by connecting a parallel impedance to the current source.

The parallel impedance may be smaller than the internal impedance of the current source.

Contact impedance values between the first, second, third and fourth electrodes and the surface of the examinee have different impedance values, respectively.

When the impedance measurer operates according to the second mode, the current source is connected between the second electrode and the fourth electrode, and the voltmeter is connected between the second electrode and the third electrode, and the first electrode is electrically disconnected from the current source.

The method may further include: switching the impedance measurer to a third mode; and measuring a third impedance value of the examinee when the impedance measurer operates according to the third mode, wherein when the impedance measurer operates according to the third mode, the current source is connected between the first electrode and the fourth electrode, and the voltmeter is connected between the first electrode and the third electrode, and the second electrode is electrically disconnected from the current source.

The method may further include: switching the impedance measurer to a fourth mode; and measuring a fourth impedance value of the examinee when the impedance measurer operates according to the fourth mode, wherein when the impedance measurer operates according to the fourth mode, the current source is connected between the first electrode and the fourth electrode, and the voltmeter is connected between the second electrode and the fourth electrode, and the third electrode is electrically disconnected from the current source.

The method may further include: switching the impedance measurer to a fifth mode; and measuring a fifth impedance value of the examinee when the impedance measurer operates according to the fifth mode, wherein when the impedance measurer operates according to the fifth mode, the current source is connected between the first electrode and the third electrode, and the voltmeter is connected between the second electrode and the third electrode, and the fourth electrode is electrically disconnected from the current source.

The obtaining of the bio impedance of the examinee may include obtaining the bio impedance of the examinee by compensating for an effect of contact impedance values between the first, second, third and fourth electrodes and the surface of the examinee in the first, second, third, fourth and fifth impedance values.

The method may further include outputting bio information of the examinee based on the bio impedance of the examinee.

The bio information of the examinee may include at least one of a body fat amount of the examinee, a basal metabolic amount of the examinee, a skeletal muscle amount of the examinee, a blood flow amount of the examinee, a breathing rate of the examinee, a heart rate of the examinee, and heart rate variation of the examinee.

According to an aspect of another exemplary embodiment, a method of measuring a bio signal using a bio signal measuring apparatus includes: positioning electrodes included as part of the bio signal measuring apparatus to contact a surface of an examinee; switching an impedance measurer included as part of the bio signal measuring apparatus and including an amperemeter, a voltmeter, and a current source, to a first mode, the current source inducing an internal impedance; measuring, by using the amperemeter, a current amount supplied from the current source to the electrodes when the impedance measurer operates according to the first mode; determining a first impedance value of the examinee based on a current amount supplied to the electrodes and a voltage measured by the voltmeter when the impedance measurer operates according to the first mode; switching the impedance measurer to a second mode; measuring, by using the amperemeter, a current amount supplied from the current source to the electrodes when the impedance measurer operates according to the second mode; determining a second impedance value of the examinee based on a current amount supplied to the electrodes and a voltage measured by the voltmeter when the impedance measurer operates according to the second mode; and obtaining bio impedance of the examinee based on the first and second impedance values.

The method may further include outputting bio information of the examinee based on the bio impedance of the examinee.

According to an aspect of another exemplary embodiment, an apparatus configured to measure a bio signal includes an electrode unit including electrodes that contact a surface of an examinee; an impedance measurer including a voltmeter and a current source, the current source inducing an internal impedance; a mode controller configured to control the impedance measurer to measure a first impedance value of the examinee while the impedance measurer is operating according to a first mode, and measure a second impedance value of the examinee while the impedance measurer is operating according to a second mode; and a bio impedance obtainer configured to obtain bio impedance of the examinee based on the first and second impedance values and the internal impedance of the current source.

The electrode unit may further include a first electrode, a second electrode, a third electrode and a fourth electrode, and the mode controller may be configured to control the impedance measurer such that the current source is connected between the first electrode and the fourth electrode, and the voltmeter is connected between the second electrode and the third electrode when the impedance measurer operates according to the first mode.

The mode controller may be configured to control the impedance measurer such that the current source is connected between the first electrode and the fourth electrode, and the voltmeter may be connected between the second electrode and the third electrode, and the first electrode and the second electrode may be short-circuited, and the third electrode and the fourth electrode may be short-circuited, when the impedance measurer operates according to the second mode.

The bio impedance obtainer may be configured to obtain the bio impedance by compensating for an effect of contact impedance between the electrodes and the surface of the examinee in the first and second impedance values by considering the internal impedance of the current source.

The bio impedance obtainer may be configured to obtain the bio impedance by using Equation 1:

$$Z_m = Z_{4P} \frac{(\beta + Z_i)(\beta + Z_S)}{Z_{4P}(2\beta + Z_i + Z_S) + Z_i Z_S} \quad \text{Equation 1}$$

where $\beta$ is defined by Equation 2, $$\beta = \frac{2}{\frac{1}{Z_{2P}} - \frac{1}{Z_i} - \frac{1}{Z_S}} \quad \text{Equation 2}$$

where $Z_{4P}$=a first impedance value, $Z_{2P}$=a second impedance value, $Z_i$=an input impedance value of the impedance measurer, and $Z_s$=the internal impedance of the current source.

The impedance measurer may further include: a current source parallel impedance that is parallel-connected to the current source and which changes an effective value of the internal impedance of the current source.

The current source parallel impedance may have an impedance value that is less than the internal impedance of the current source.

Contact impedance values between the first, second, third and fourth electrodes and the surface of the examinee have different impedance values, respectively.

The mode controller may be configured to control the impedance measurer such that when the impedance measurer operates according to the second mode, the current source is connected between the second electrode and the fourth electrode, and the voltmeter is connected between the second electrode and the third electrode, and the first electrode is electrically disconnected from the current source.

The mode controller may control the impedance measurer to measure a third impedance value of the examinee when the impedance measurer operates according to a third mode, and may control the impedance measurer such that when the impedance measurer operates according to the third mode, the current source is connected between the first electrode and the fourth electrode, and the voltmeter is connected between the first electrode and the third electrode, and the second electrode is electrically disconnected from the current source.

The mode controller may control the impedance measurer to measure a fourth impedance value of the examinee when the impedance measurer operates according to a fourth mode, and may control the impedance measurer such that when the impedance measurer operates according to the fourth mode, the current source is connected between the first electrode and the fourth electrode, and the voltmeter is connected between the second electrode and the fourth electrode, and the third electrode may be electrically disconnected from the current source.

The mode controller may control the impedance measurer to measure a fifth impedance value of the examinee when the impedance measurer operates according to a fifth mode, and may control the impedance measurer such that when the impedance measurer operates according to the fifth mode, the current source is connected between the first electrode and the third electrode, and the voltmeter is connected between the second electrode and the third electrode, and the fourth electrode is electrically disconnected from the current source.

The bio impedance obtainer may be configured to obtain the bio impedance by compensating for an effect of the contact impedance between the first, second, third and fourth electrodes and the surface of the examinee in the first, second, third, fourth and fifth impedance values.

The apparatus may further include a bio information outputter configured to output bio information of the examinee based on the bio impedance of the examinee.

The bio information of the examinee may include at least one of a body fat amount of the examinee, a basal metabolic amount of the examinee, a skeletal muscle amount of the examinee, a blood flow amount of the examinee, a breathing rate of the examinee, a heart rate of the examinee, and heart rate variation of the examinee.

According to an aspect of another exemplary embodiment, an apparatus configured to measure a bio signal includes: an electrode unit comprising electrodes that contact a surface of an examinee; an impedance measurer including a voltmeter, a current source inducing an internal impedance, and an amperemeter provided between the current source and the electrode unit and configured to measure a current amount supplied from the current source to the electrode unit; a mode controller configured to control the impedance measurer to measure a first impedance value of the examinee while the impedance measurer operates according to a first mode, and measure a second impedance value of the examinee while the impedance measurer operates according to a second mode; and a bio impedance obtainer configured to obtain bio impedance of the examinee based on the first and second impedance values.

The first impedance value may be determined by a voltage value measured by the voltmeter and a current value measured by the amperemeter when the impedance measurer operates according to the first mode, and the second impedance value may be determined by a voltage value measured by the voltmeter and a current value measured by the amperemeter when the impedance measurer operates according to the second mode.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Exemplary embodiments are described below with reference to the accompanying drawings.

As the terms used herein, so far as possible, widely-used general terms are selected in consideration of functions in the exemplary embodiments; however, these terms may vary according to the intentions of those of ordinary skill in the art, the precedents, or the appearance of new technology. Also, in some cases, there may be terms that are arbitrarily selected by the applicant, and the meanings thereof will be described in detail in the corresponding portions of the description of the exemplary embodiments. Therefore, the terms used herein are not simple titles of terms and should be defined based on the meanings thereof and the overall description of the exemplary embodiments.

It will be understood that when a component is referred to as being "connected" to another component, the component may be "directly connected" to the other component or may be "electrically connected" to the other component with the other component interposed therebetween. It will be understood that the terms "comprises", "includes", and "has", when used herein, specify the presence of stated elements, but do not preclude the presence or addition of other elements, unless otherwise defined. Also, the terms "unit" and "module" used herein represent a unit for processing at least one function or operation, which may be implemented by hardware, software, or a combination of hardware and software.

The terms "configure" and/or "comprise" used herein should not be construed as necessarily including all components or operations described in the specification, but should be construed as not including some components or operations or further including additional components or operations.

It will be understood that although the terms "first", "second", etc., may be used herein to describe various components, these components should not be limited by these terms. These components are only used to distinguish one component from another.

Descriptions of exemplary embodiments below should not be construed as limiting the scope of the exemplary embodiments, and concepts that are easily inferred by a person of ordinary skill in the art should be construed as falling within the scope of exemplary embodiments. Hereinafter, certain exemplary embodiments provided for exemplary purposes only are described below with reference to the accompanying drawings.

Figure 1:
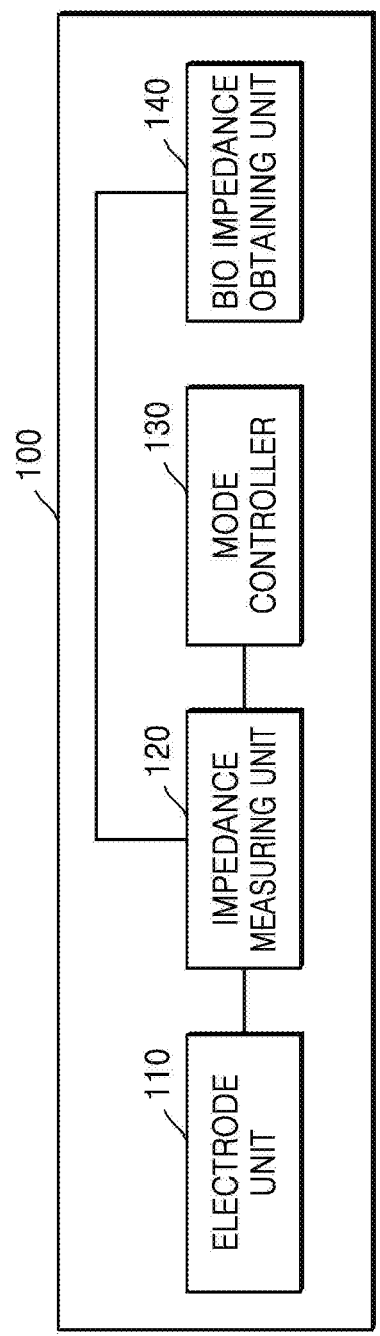
FIG. 1 is a block diagram illustrating an apparatus for measuring a bio signal according to an exemplary embodiment.

FIG. 1 is a block diagram illustrating an apparatus 100 for measuring a bio signal according to an exemplary embodiment.

Referring to FIG. 1, the apparatus 100 for measuring a bio signal according to an exemplary embodiment may include an electrode unit 110, an impedance measuring unit (e.g., impedance measurer) 120, a mode controller 130, and a bio impedance obtaining unit (e.g., bio impedance obtainer) 140.

The electrode unit 110 may include at least two electrodes. In the case where the apparatus 100 for measuring a bio signal is a wearable device such as a smart watch, the electrodes of the electrode unit 110 may contact a user's body when the user wears the wearable device. One of the electrodes of the electrode unit 110 may contact the user's body when the user wears the wearable device, and the other of the electrodes may contact the user's body due to the user's motion.

The impedance measurer 120 measures impedance of an electric circuit including the body by using a bio impedance analyzer (BIA) method. The impedance measurer 120 may apply a current via a first electrode 110a of the electrode unit 110, and measure a voltage between the electrodes of the electrode unit 110. The impedance measurer 120 may measure the impedance of the electric circuit by measuring voltages between the electrodes.

The mode controller 130 may change a connection mode of an internal circuit of the impedance measurer 120. When the mode controller 130 changes the connection mode of the internal circuit of the impedance measurer 120, an impedance value measured by the impedance measurer 120 may change.

The bio impedance obtainer 140 may measure bio impedance of an examinee by using impedance values measured by the impedance measurer 120. According to an exemplary embodiment, the examinee refers to a living body (e.g., human) that wears the apparatus 100 for measuring a bio signal, and may include a human body or a biological tissue of an animal. The bio impedance obtainer 140 may obtain a bio impedance value, regardless of contact impedance between the electrodes of the electrode unit 110 and the examinee, based on the impedance values measured by the impedance measurer 120.

Figure 2:
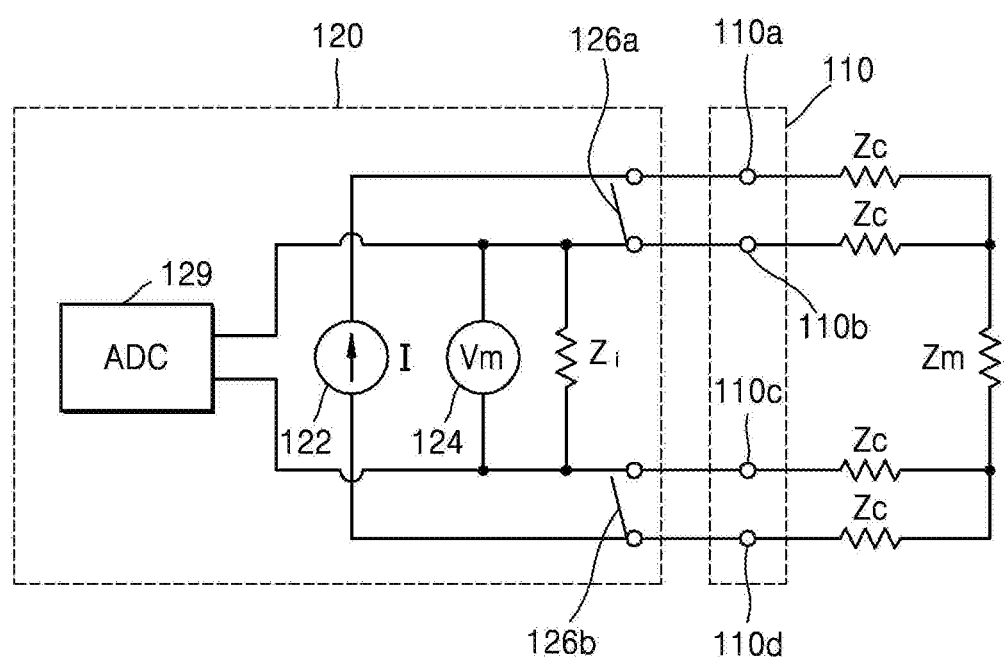
FIG. 2 is an exemplary circuit diagram illustrating an impedance measurer and an electrode unit according to a first mode.

FIG. 2 is an exemplary circuit diagram illustrating an impedance measurer 120 and an electrode unit 110. An internal circuit configuration of the impedance measurer 120 may be changed by the mode controller 130. A circuit connection state of the impedance measurer 120 illustrated in FIG. 2 is referred to as a first mode.

In FIG. 2, Zc represents contact impedance between electrodes 110a, 110b, 110c, and 110d, and an examinee. Zm represents bio impedance of the examinee. Zi represents impedance of an analog front end (AFE), and the AFE represents the impedance measurer 120. A current source 122 may generate a constant current. At least a portion of a current generated by the current source 122 may be applied to the examinee via the electrodes 110a and 110d of the electrode unit 110. A voltmeter 124 may measure a voltage Vm between the second electrodes 110b and the third electrode 110c. A voltage measured by the voltmeter 124 is output to an analog-to-digital converter (ADC) 129. The ADC 129 may convert a voltage input as an analog signal into a digital signal. An impedance value measured by the impedance measurer 120 may be determined from a voltage value measured by the voltmeter 124 of the impedance measurer 120. For example, a first impedance value $Z_{4P}$ measured by the impedance measurer 120 under the first mode may be determined by dividing a voltage Vm measured by the voltmeter 124 based on a output current value of the current source 122. The first impedance value $Z_{4P}$ may be expressed by Equation 1.

$$Z_{4P} = f_1(Z_m, Z_c, Z_i) = Z_m \frac{1}{1 + \frac{Z_m + 2Z_c}{Z_i}} \quad \text{Equation 1}$$

Since Zi is a value determined by a circuit characteristic and the first impedance value $Z_{4P}$ is a value obtained by measurement in Equation 1, there are two unknowns Zm and Zc. To obtain the two unknowns, another equation is required. The mode controller 130 may switch a circuit connection of the impedance measurer 120 to a second mode by adjusting an internal switch 126 of the impedance measurer 120.

Figure 3:
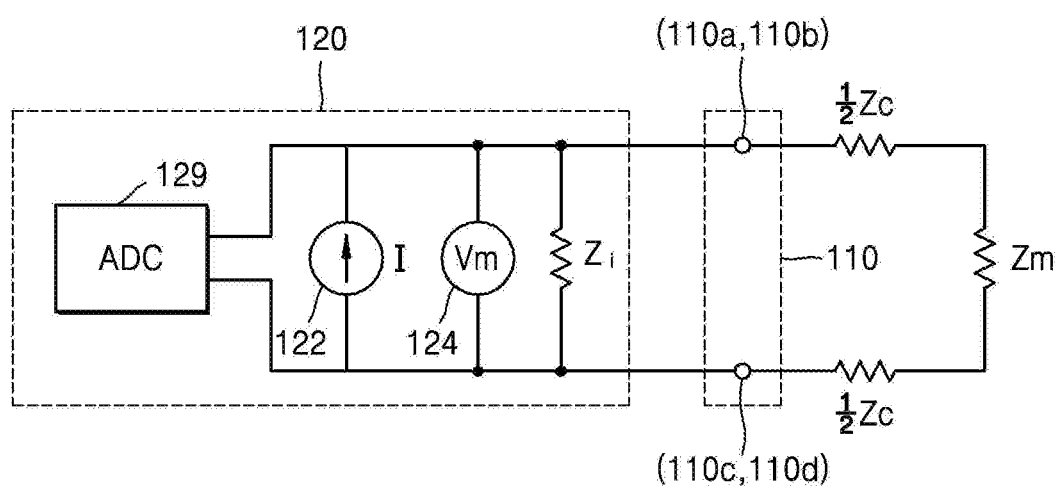
FIG. 3 is an exemplary circuit diagram illustrating an impedance measurer and an electrode unit according to a second mode.

FIG. 3 is an exemplary circuit diagram illustrating the impedance measurer 120 and the electrode unit 110 according to a second mode.

Referring to FIG. 3, in the second mode, the first electrode 110a and the second electrode 110b may be short-circuited. Also, under the second mode, the third electrode 110c and the fourth electrode 110d may be short-circuited. The mode controller 130 may adjust switches 126a and 126b inside the impedance measurer 120 in order to switch the internal circuit connection of the impedance measurer 120 to the second mode. As an example, the mode controller 130 may switch the first switch 126a and the second switch 126b of the impedance measurer 120 to a closed state when operating in the second mode. When the first switch 126a becomes a closed state, the first electrode 110a and the second electrode 110b may be short-circuited. Also, when the second switch 126b becomes a closed state, the third electrode 110c and the fourth electrode 110d may be short-circuited. It is understood that the configuration of the switches and electrodes may be modified from the configuration shown in FIGS. 2 and 3.

A second impedance value $Z_{2P}$ may be determined from a voltage value Vm measured by the voltmeter 124 under the second mode. For example, the second impedance value $Z_{2P}$ may be obtained by dividing the voltage value Vm measured by the voltmeter 124 by an output current value of the current source 122 under the second mode.

The second impedance value $Z_{2P}$ measured by the impedance measurer 120 may be expressed by Equation 2.

$$Z_{2P} = f(Z_m, Z_c, Z_i) = \frac{1}{\frac{1}{Z_m + 2Z_c} + \frac{1}{Z_i}} \quad \text{Equation 2}$$

In Equations 1 and 2, $Z_{4P}$ and $Z_{2P}$ are measured values, and Zi is a value determined depending on a characteristic of the AFE. Therefore, since there are two unknown variables Zm and Cz and two equations 1 and 2, Zm and Zc may be calculated by simultaneously solving Equations 1 and 2, and even when a value of Zc is not known or not calculated, Zm may be calculated.

Measurement values of the first and second impedance values $Z_{4P}$ and $Z_{2P}$ expressed by Equations 1 and 2 are values obtained by dividing a voltage Vm measured by the voltmeter 124 by a current I of the amperemeter 122. However, the current I of the amperemeter 122 may not be entirely transferred to the electrode unit 110 because, in contrast to an ideal amperemeter, the real amperemeter 122 includes an internal impedance and thus may not always supply a constant current to the electrode unit 110. The internal impedance may be generated (induced) for various reasons. For example, the internal impedance may be generated (induced) as a result of parasitic components of the current source 122, other electrical components of the current source 122, a combination thereof, or for different reasons altogether. There may be many different causes of the internal impedance.

Figure 4:
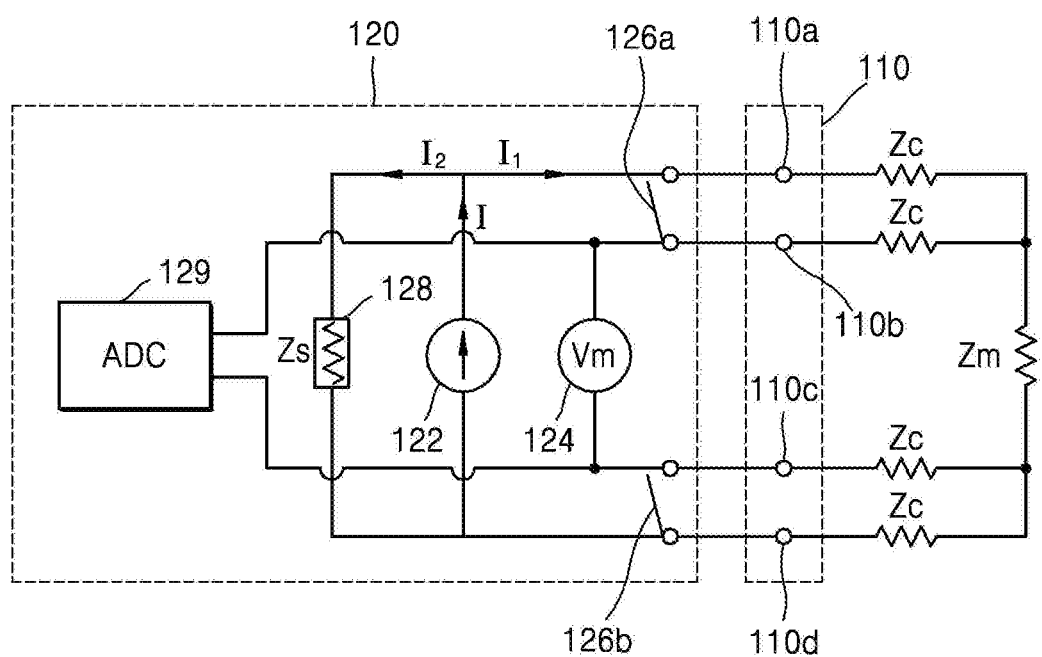
FIG. 4 is a circuit diagram illustrating the impedance measurer according to the first mode illustrated in FIG. 2 when taking into account an internal impedance of a current source.

FIG. 4 is a circuit diagram illustrating the impedance measurer 120 according to the first mode illustrated in FIG. 2 by taking into account an internal impedance of the current source 122.

Referring to FIG. 4, the impedance measurer 120 may include an internal impedance Zs parallel-connected to the current source 122. A current I coming from the current source 122 may be divided into a current $I_2$ flowing through the internal impedance Zs and a current $I_1$ flowing toward the electrode unit 110. In the case where the magnitude of contact impedance Zc between the electrodes 110a, 110b, 110c, and 110d of the electrode unit 110 and an examinee is considerably less than the internal impedance Zs, the magnitude of the current $I_1$ may be considerably larger than that of the current $I_2$. In this case, it is considered that the current $I_1$ flowing toward the electrode unit 110 is almost the same as the value of the output current I of the current source 122. Therefore, in this case, there may not be a significant problem in accurately obtaining bio impedance Zm even without taking into account the internal impedance Zs.

However, when the areas of the electrodes 110a, 110b, 110c, and 110d are reduced, the magnitude of the contact impedance Zc may increase. When the magnitude of the contact impedance Zc increases, the magnitude of the current $I_1$ may become similar to or less than the magnitude of the current $I_2$. In this case, there may be a substantial difference between the current $I_1$ supplied to the electrode unit 110 and the output current I of the amperemeter 122. When a difference between the current $I_1$ supplied to the electrode unit 110 and the output current I of the amperemeter 122 increases, the accuracy of the bio impedance value Zm obtained by using Equations 1 and 2 may be reduced.

When obtaining the bio impedance Zm from the first and second impedances $Z_{4P}$ and $Z_{2P}$, the bio impedance obtainer 140 may increase the accuracy of the bio impedance value Zm by taking into account the internal impedance Zs 128. When taking into account the internal impedance Zs, the circuit diagram according to the first mode illustrated in FIG. 2 may be converted into the circuit diagram of FIG. 4. Also, the Equation used to express the first impedance $Z_{4P}$ may be changed from Equation 1 to Equation 3 below.

$$Z_{4P} = Z_m \times \frac{1}{1 + \frac{Z_m + 2Z_c}{Z_1}} \times \frac{Z_s}{Z_s + 2Z_c + \frac{1}{\frac{1}{Z_m} + \frac{1}{2Z_c + Z_i}}} \quad \text{Equation 3}$$

Referring to Equation 3, it is shown that the first impedance $Z_{4P}$ includes a factor that depends on the internal impedance Zs. In this case, the last factor from among the multiplication factors in Equation 3 may almost converge to 1 when $Z_a \gg Z_c$. In this case, Equation 3 becomes equal to Equation 1. However, when the sizes of the electrodes 110a, 110b, 110c, and 110d of the electrode unit 110 are reduced, the condition of $Z_s \gg Z_c$ may not be satisfied. Further, when the condition of $Z_s \gg Z_c$ is not satisfied, Equation 1 and Equation 3 become different from each other. Therefore, when the apparatus 100 for measuring a bio signal is miniaturized, an influence of the internal impedance Zs of the current source 122 may increase.

The mode controller 130 may switch the impedance measurer 120 to the second mode by switching the first switch 126a and the second switch 126b of the impedance measurer 120 to a closed state. When taking into account the internal impedance 128, the circuit diagram according to the second mode illustrated in FIG. 3 may be changed into the circuit diagram of FIG. 5.

Figure 5:
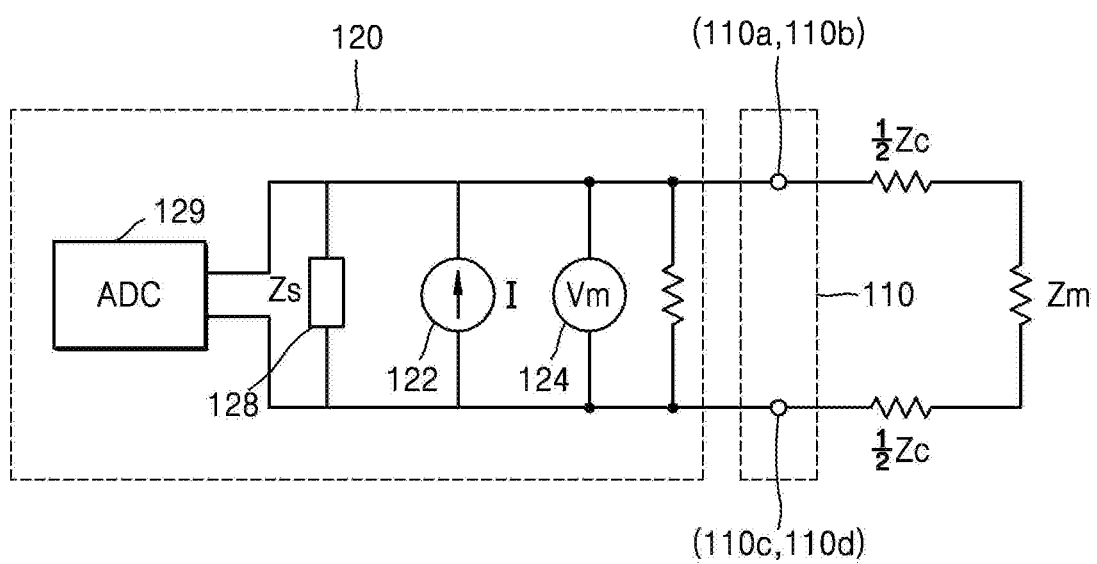
FIG. 5 is a circuit diagram illustrating an impedance measurer and an electrode unit according to a second mode when taking into account an internal impedance.

FIG. 5 is a circuit diagram illustrating the impedance measurer 120 and the electrode unit 110 according to the second mode when taking into account an internal impedance Zs.

Referring to FIG. 5, the first electrode 110a and the second electrode 110b are short-circuited and may be treated as one electrode. In this case, contact impedance between the first electrode 110a and an examinee and contact impedance between the second electrode 110b and the examinee are parallel-connected and thus may be treated as one contact impedance (½×Zc). Also, the third electrode 110c and the fourth electrode 110d are short-circuited and may be treated as one electrode. In this case, contact impedance between the third electrode 110c and the examinee and contact impedance between the fourth electrode 110d and the examinee are parallel-connected and thus may be treated as one contact impedance (½×Zc). The second impedance $Z_{2P}$ measured according to the second mode illustrated in FIG. 5 may be expressed by Equation 4.

$$Z_{2P} = \frac{1}{\frac{1}{Z_m + Z_c} + \frac{1}{Z_i} + \frac{1}{Z_s}} \qquad \text{Equation 4}$$

In Equations 3 and 4, $Z_{4P}$ and $Z_{2P}$ are measured values, and Zi is a value determined depending on a characteristic of the AFE. Therefore, Zm and Zc may be calculated by simultaneously solving Equations 3 and 4, and even when a value of Zc is not known or not calculated, Zm may be calculated.

The impedance measurer 120 may transfer information regarding a measurement result of the first impedance value $Z_{4P}$ and a measurement result of the second impedance value $Z_{2P}$ to the bio impedance obtainer 140. Exemplarily, the ADC 129 of the impedance measurer 120 may convert a voltage value measured by the voltmeter 124 into a digital signal and transmit the digital signal to the bio impedance obtainer 140. Since the magnitude of an output current of the current source 122 is constant, the bio impedance obtainer 140 may obtain the first and second impedance values $Z_{4P}$ and $Z_{2P}$ from the transmitted voltage value. As another example, the ADC 129 may convert a value obtained by dividing a voltage value measured by the voltmeter 124 by an output current value of the current source 122 into a digital signal and transmit the digital signal to the bio impedance obtainer 140.

The bio impedance obtainer 140 may obtain the bio impedance Zm from the first impedance value $Z_{4P}$, the second impedance value $Z_{2P}$, and the internal impedance Zs.

Figure 6:
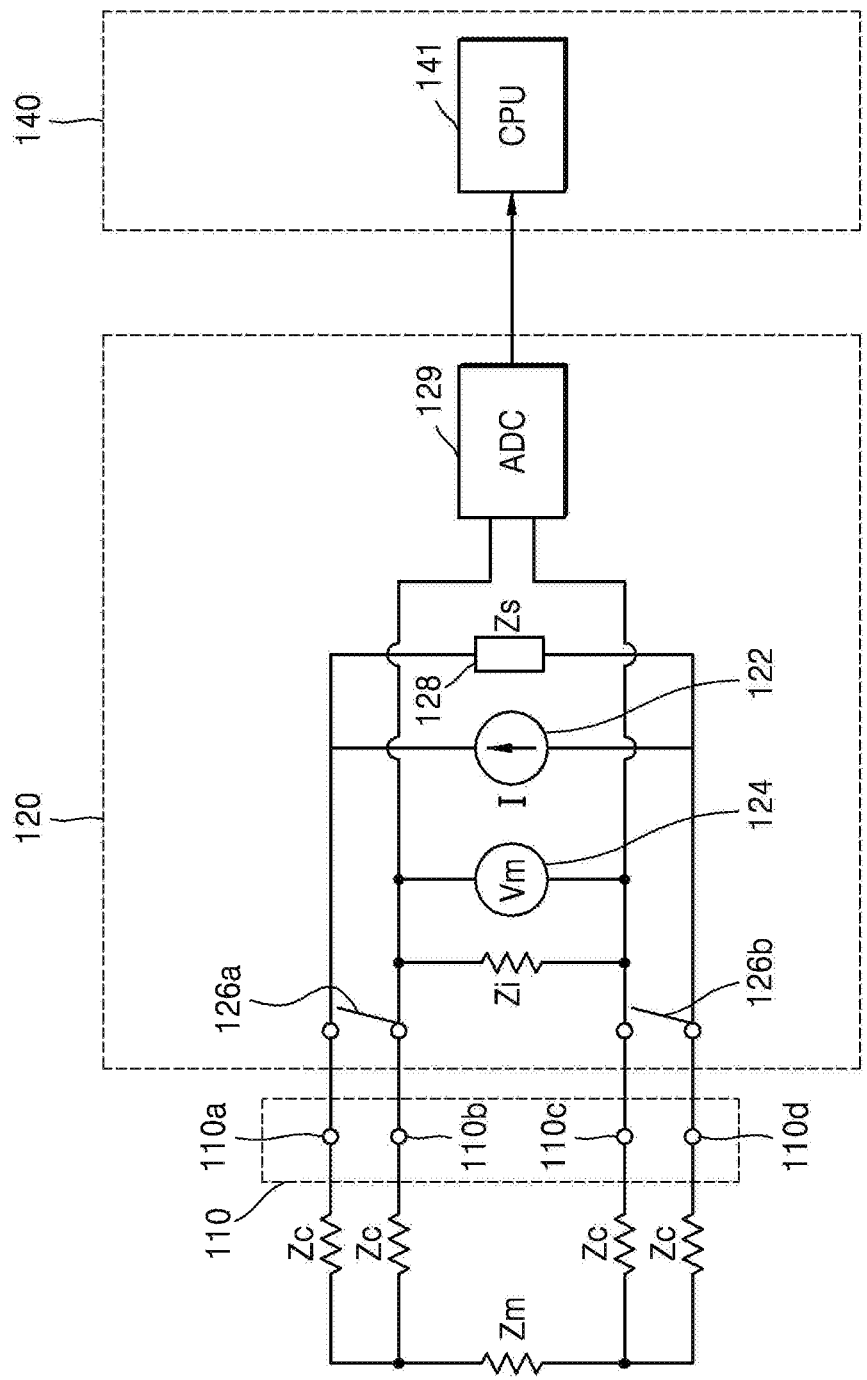
FIG. 6 is a circuit diagram for explaining an apparatus for measuring a bio signal according to an exemplary embodiment.

FIG. 6 is a circuit diagram for explaining an apparatus 100 for measuring a bio signal according to an exemplary embodiment.

Referring to FIG. 6, the ADC 129 of the impedance measurer 120 may convert the magnitude of a measured voltage or an impedance value obtained from the magnitude of the voltage into a digital signal and transfer the digital signal to the bio impedance obtainer 140. The bio impedance obtainer 140 may include a central processing unit (CPU) 141 for calculating bio impedance Zm. The CPU 141 may calculate the bio impedance Zm by simultaneously solving Equations 3 and 4. Exemplarily, the CPU 141 of the bio impedance obtainer 140 may calculate the bio impedance Zm by using Equation 5.

$$Z_m = Z_{4P} \frac{(\beta + Z_i)(\beta + Z_S)}{Z_{4P}(2\beta + Z_i + Z_S) + Z_i Z_S} \qquad \text{Equation 5}$$

In Equation 5, β may be defined by Equation 6 below.

$$\beta = \frac{2}{\frac{1}{Z_{2P}} - \frac{1}{Z_i} - \frac{1}{Z_S}} \qquad \text{Equation 6}$$

As another example, the bio impedance obtainer 140 may obtain the bio impedance Zm by using a lookup table or other predetermined information source) without directly calculating the bio impedance Zm. For example, the bio impedance Zm may be stored internally by the bio impedance obtainer 140, may be received from an external source over a network connection (e.g., over the Internet or a LAN), etc.

Figure 7:
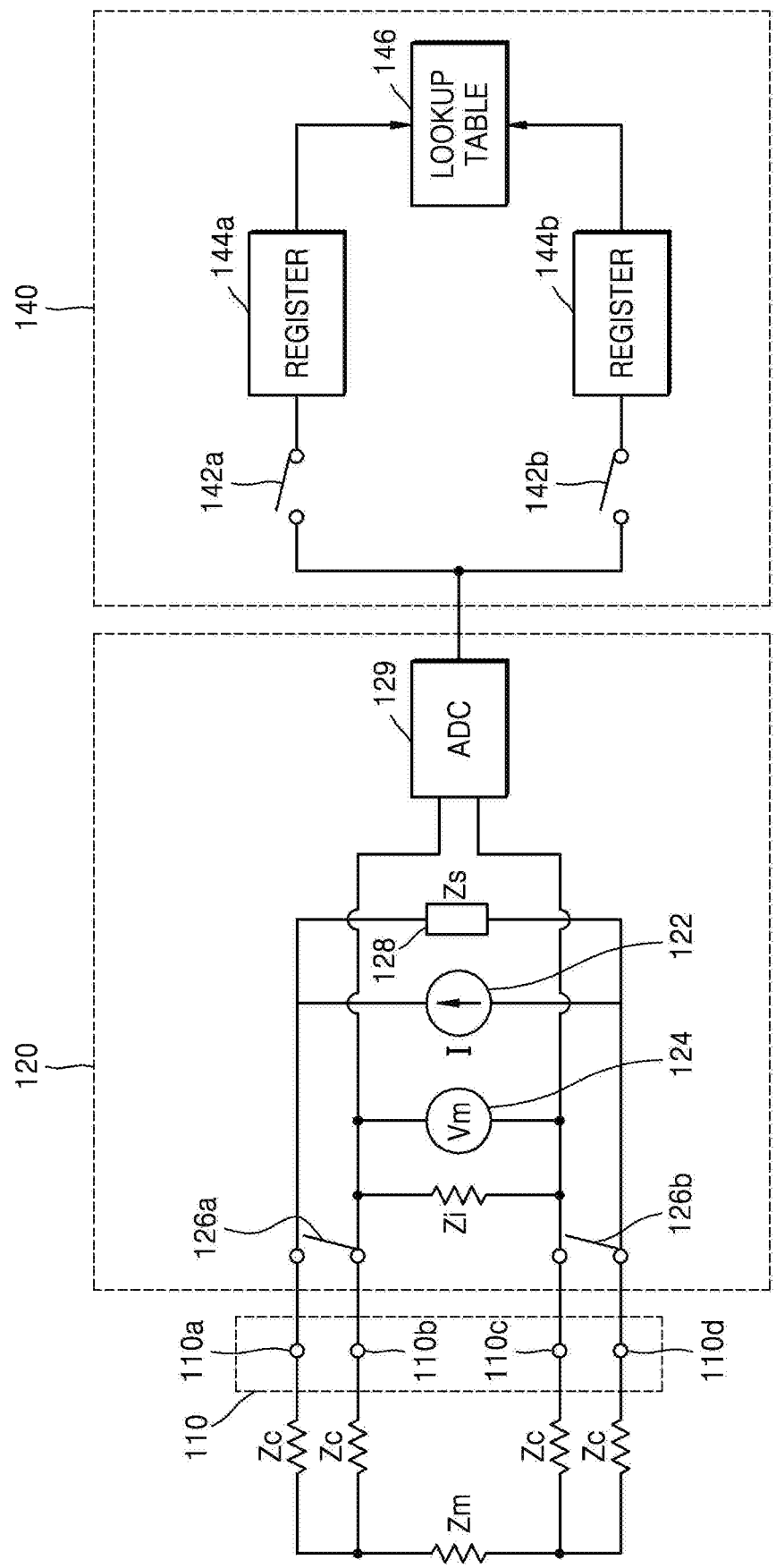
FIG. 7 is another circuit diagram for explaining an apparatus for measuring a bio signal according to an exemplary embodiment.

FIG. 7 is another circuit diagram for explaining an apparatus 100 for measuring a bio signal according to an exemplary embodiment.

Referring to FIG. 7, the bio impedance obtainer 140 may obtain bio impedance by using a lookup table 146.

The bio impedance obtainer 140 may include two switches 142a and 142b, two registers 144a and 144b, and the lookup table 146. Whether the two switches 142a and 142b are connected may be determined depending on a state of the impedance measurer 120. For example, when the impedance measurer 120 is operating according to the first mode, the upper switch 142a is closed, and the lower switch 142b may be open. Also, when the impedance measurer 120 is operating according to the second mode, the upper switch 142a may be open and the lower switch 142b may be closed.

The registers 144a and 144b store a voltage value or an impedance value. For example, a voltage value or an impedance value measured during operation of the first mode may be stored in the upper register 144a, and a voltage value or an impedance value measured during operation of the second mode may be stored in the lower register 144b.

The lookup table 146 may receive values of a voltage or impedance stored in the registers 144a and 144b and output bio impedance. For example, when values of two voltages are input, the lookup table 146 may determine a value corresponding to the two voltage values. As another example, when the first and second impedance values $Z_{4P}$ and $Z_{2P}$ are input, the lookup table 146 may determine a value corresponding to the first and second impedance values $Z_{4P}$ and $Z_{2P}$.

The determined value represents bio impedance. For example, the lookup table 146 may store a 2×2-table regarding values of two voltages. As another example, the lookup table 146 may store a 2×2-table regarding the first and second impedance values $Z_{4P}$ and $Z_{2P}$.

A horizontal axis may represent a voltage or a first impedance value $Z_{4P}$ measured according to the first mode, and a vertical axis may represent a voltage or a second impedance value $Z_{2P}$ measured according to the second mode. When a value of the horizontal axis and a value of the vertical axis are determined, the lookup table 146 may determine bio impedance Zm corresponding to the value of the horizontal axis and the value of the vertical axis.

Figure 8:
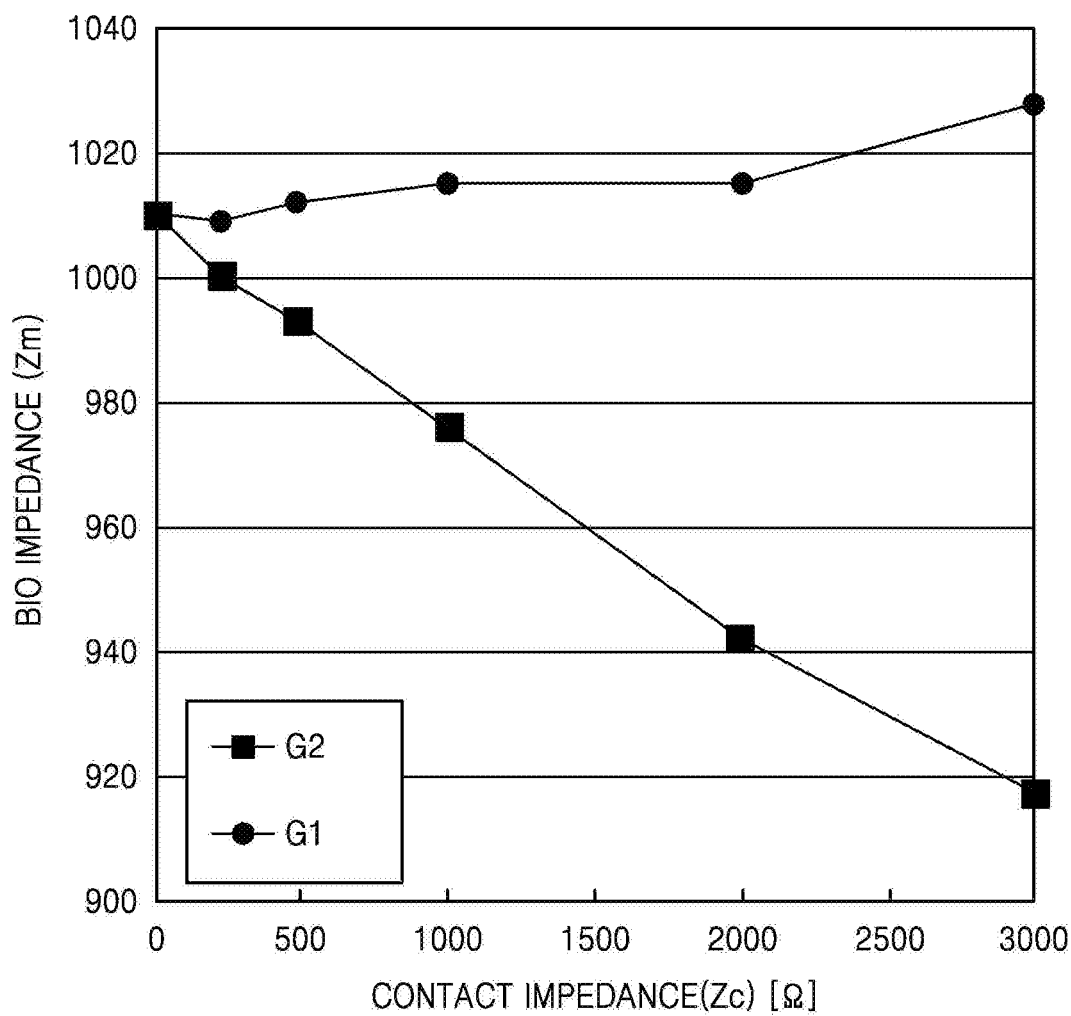
FIG. 8 is a graph illustrating experiment results that compare the case of taking into account an internal impedance of a current source with the case of not taking into account an internal impedance of a current source.

FIG. 8 is a graph illustrating experiment results that compare the case of taking into account an internal impedance Zs of a current source 122 with the case of not taking into account the internal impedance Zs of the current source 122.

In FIG. 8, a horizontal axis represents a contact impedance value Zc between the electrodes 110a, 110b, 110c, and 110d, and a surface of an examinee. Also, a vertical axis represents an obtained bio impedance value Zm. FIG. 8 represents results of measuring the same bio impedance Zm (about 1 kΩ) while changing the magnitude of contact impedance Zc. According to an experiment shown in FIG. 9, Zi=2 MΩ and Zs=50 kΩ have been set. A graph G1 of FIG. 8 represents results of obtaining bio impedance Zm by taking into account internal impedance Zs according to an exemplary embodiment. A graph G2 represents results of obtaining bio impedance Zm without taking into account the internal impedance.

Referring to FIG. 8, the graph G2 shows that when a contact impedance value Zc gradually increases, an obtained bio impedance value Zm gradually decreases. Even though the experiment has been performed on the same examinee, when not taking into account the internal impedance Zs of the current source 122, the obtained bio impedance value Zm may differ from an actual value depending on the contact impedance value Zc. For example, an error rate between a bio impedance value Zm obtained by the graph G2 while contact impedance Zc is 3 KΩ and an actual value is about 10.2%.

Unlike the graph G2, the graph G1 shows that an obtained bio impedance value Zm is almost constant regardless of contact impedance value Zc. That is, when the bio impedance Zm is obtained by taking into account the internal impedance Zs, the accuracy of the obtained bio impedance value Zm may be high even when contact impedance Zc is large. For example, an error rate between a bio impedance value Zm obtained by the graph G1 while contact impedance Zc is 3 KΩ and an actual value is merely about 1.7%.

In the above explanation, a principle in which the apparatus 100 for measuring a bio signal measures bio impedance Zm according to an exemplary embodiment has been described with reference to FIGS. 4 to 8. According to the above-described exemplary embodiments, the apparatus 100 for measuring a bio signal may measure the first and second impedance values $Z_{4P}$ and $Z_{2P}$ from the examinee while changing the mode of the impedance measurer 120. Also, the apparatus 100 for measuring a bio signal may remove an unwanted effect of the contact impedance Zc from the first and second impedance values $Z_{4P}$ and $Z_{2P}$, and obtain the bio impedance Zm of the examinee. The apparatus 100 for measuring a bio signal may obtain the bio impedance Zm by taking into account the internal impedance Zs of the current source 122. By doing so, the apparatus 100 for measuring a bio signal may obtain the bio impedance value Zm with high accuracy regardless of the contact impedance value Zc.

In the above description, the internal impedance Zs parallel-connected to the current source 122 has been treated as an already known constant value. However, the internal impedance Zs may change depending on the magnitude of a voltage applied to both ends of the current source 122. The reason why the internal impedance Zs changes is that an output characteristic of an internal device of the current source 122 may change depending on the magnitude of a voltage applied to both ends of the current source 122. Exemplarily, the current source 122 may include a plurality of transistors. An ideal transistor may maintain the constant magnitude of an output current in a saturation region. However, in an actual transistor, a ratio of a voltage and a current may gradually change in the saturation region.

Figure 9:
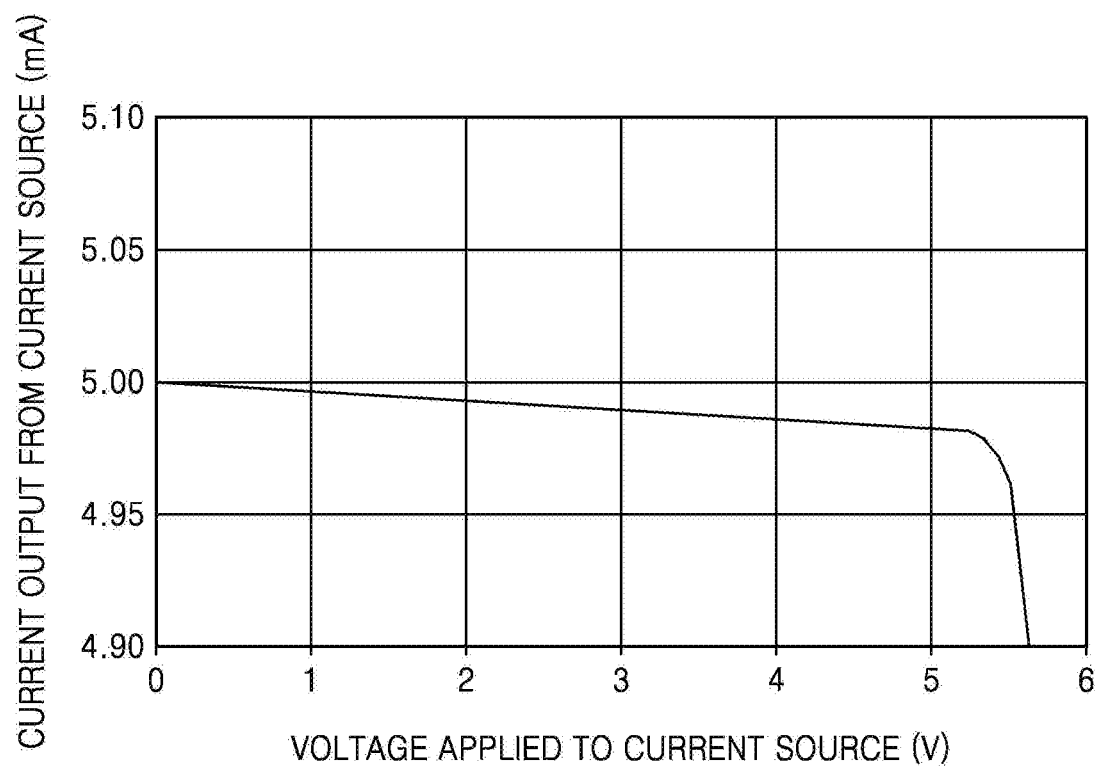
FIG. 9 is a graph illustrating a relation between a voltage applied to a current source and an output current of the current source.

FIG. 9 is a graph illustrating relation between a voltage applied to a current source 122 and an output current of the current source 122.

In FIG. 9, a horizontal axis represents a voltage applied to both ends of the current source 122, and a vertical axis represents an output current of the current source 122. Referring to FIG. 9, as a voltage applied to both ends of the current source 122 increases, an output current of the current source 122 gradually changes, and when the voltage exceeds a threshold, the output current is rapidly reduced. In a section in which the output current is rapidly reduced, it is understood that a transistor of the current source 122 has reached a breakdown region. In contrast, in a section in which the output current gradually changes, the transistor of the current source 122 is operating in the saturation region. For a voltage value used for an experiment, a voltage value in the saturation region may be used.

Unlike an ideal transistor, in an actual transistor, an output current value may slightly change due to a change of a voltage value in the saturation region. As a result, an output current of the current source 122 may change due to a change of a voltage value applied to both ends of the current source 122. This effect may be considered as an equivalent of changing the internal impedance Zs parallel-connected to the current source 122. Therefore, the bio impedance obtainer 140 may improve the accuracy of an obtained bio impedance value Zm by setting the internal impedance value Zs differently depending on a voltage applied to the current source 122 when obtaining the bio impedance value Zm.

However, setting the internal impedance value Zs differently every time the circuit operates, as described above, may be a considerably inconvenient operation. The impedance measurer 120 may further include a current source parallel impedance that is parallel-connected to the current source 122 and changes an effective value of the internal impedance Zs of the current source 122.

Figure 10:
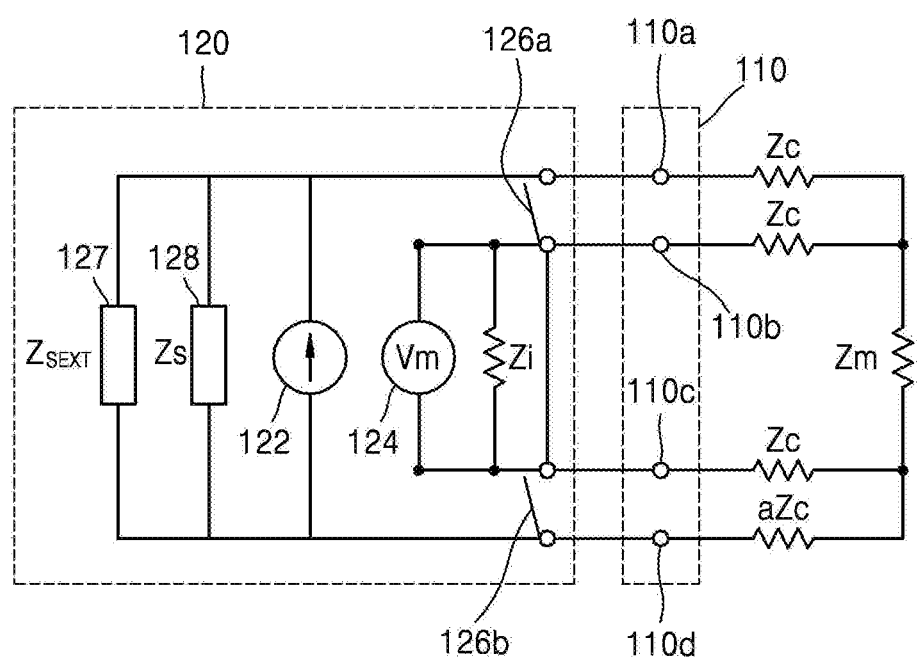
FIG. 10 is another circuit diagram for explaining an apparatus for measuring a bio signal according to an exemplary embodiment.

FIG. 10 is another circuit diagram for explaining an apparatus 100 for measuring a bio signal according to an exemplary embodiment.

Referring to FIG. 10, the impedance measurer 120 may further include a current source parallel impedance $Z_{SEXT}$ 127 that is parallel-connected to the current source 122 and changes an effective value of the internal impedance Zs of the current source 122. In the circuit diagram illustrated in FIG. 10, the internal impedance Zs of the current source 122 and the current source parallel impedance $Z_{SEXT}$ may be synthesized in parallel. Therefore, an effective value of the internal impedance of the current source 122 may change. The changed effective value of the internal impedance may be expressed by Equation 7.

$$Z_{SEFF} = \frac{Z_S Z_{SEXT}}{Z_S + Z_{SEXT}} \quad \text{Equation 7}$$

In Equation 7, $Z_{SEFF}$ is an effective value of the internal impedance of the current source 122, and is a synthesized impedance of the internal impedance Zs and the current source parallel impedance $Z_{SEXT}$.

When the internal impedance Zs changes, an amount of change in the effective value $Z_{SEFF}$ of the internal impedance Zs may be less than an amount of change in the internal impedance Zs. A rate of change in the effective value $Z_{SEFF}$ of the internal impedance Zs with respect to a change in the internal impedance Zs may be expressed by Equation 8.

$$\frac{dZ_{SEFF}}{dZ_S} = \left(\frac{Z_{SEXT}}{Z_S + Z_{SEXT}}\right)^2 \quad \text{Equation 8}$$

Equation 8 shows that a value of $$\frac{dZ_{SEFF}}{dZ_S}$$

is always less than 1. This result thus indicates that an amount of change in the effective value $Z_{SEFF}$ of the internal impedance Zs is less than an amount of change in the internal impedance Zs. Furthermore, according to Equation 8, when a value of the current source parallel impedance $Z_{SEXT}$ is small, the value of $$\frac{dZ_{SEFF}}{dZ_S}$$

becomes smaller to a greater degree. However, when the value of the current source parallel impedance $Z_{SEXT}$ is too small, a current amount supplied to the electrode unit 110 may be insufficient. Therefore, the value of the current source parallel impedance $Z_{SEXT}$ may be appropriately adjusted so that the current amount supplied to the electrode unit 110 is not insufficient while a rate of change in the effective value $Z_{SEFF}$ of the internal impedance Zs is maintained to be small (e.g., smaller than a predetermined threshold). For example, the magnitude of the current source parallel impedance $Z_{SEXT}$ may be less than that of the internal impedance Zs.

Figure 11:
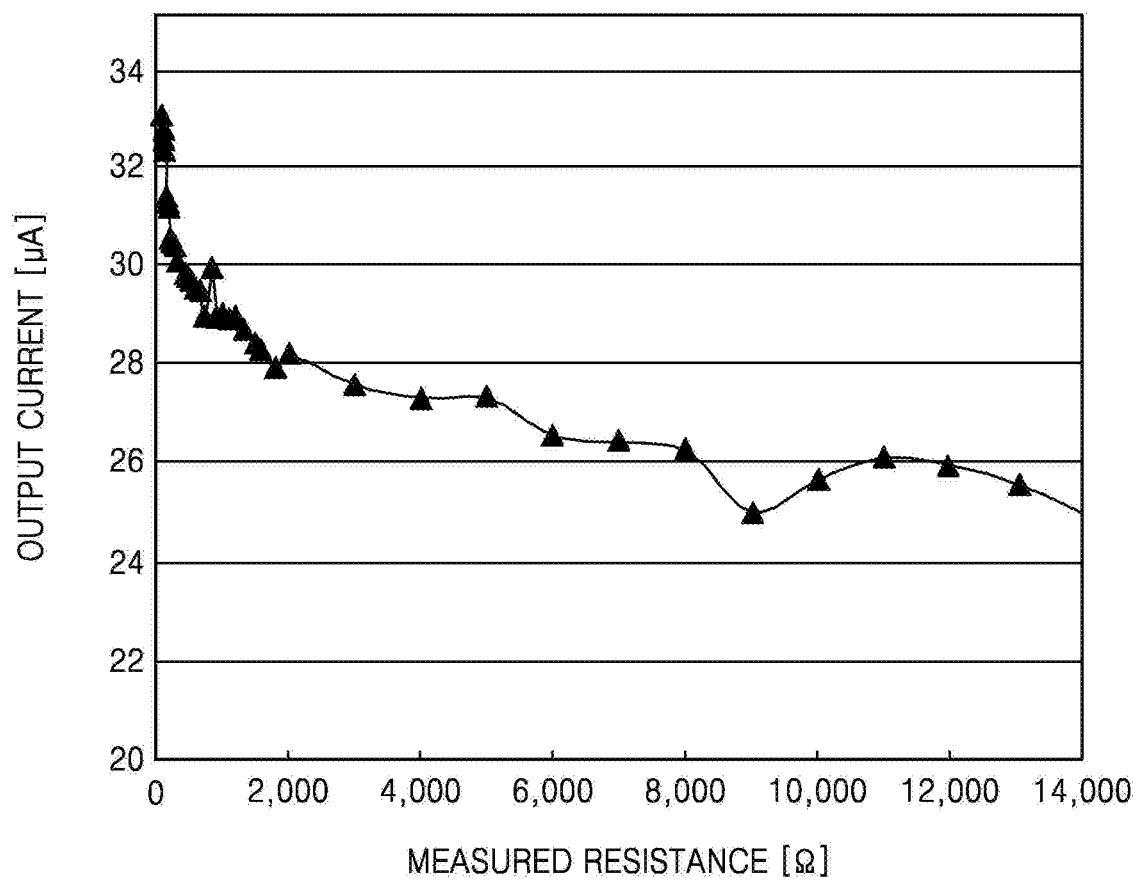
FIG. 11 is a graph illustrating a change of a current amount supplied to an electrode unit depending on a change of a first impedance value without a current source parallel impedance.

FIG. 11 is a graph illustrating a change of a current amount supplied to an electrode unit 110, where the change of the current amount depends on a change of the first impedance value $Z_{4P}$ without the current source parallel impedance $Z_{SEXT}$ 127.

In FIG. 11, a horizontal axis represents the magnitude of the first impedance value $Z_{4P}$ measured by the impedance measurer 120. A vertical axis represents a current $I_1$ (see FIG. 4) supplied to the electrode unit 110 from among a current output from the current source 122.

Referring to FIG. 11, it is shown that when the magnitude of the first impedance value $Z_{4P}$ increases, the magnitude of the current supplied to the electrode unit 110 changes irregularly. This result is because the internal impedance Zs of the current source 122 changes irregularly. Therefore, to compensate for this irregularity, the bio impedance obtainer 140 should set the internal impedance Zs of the current source 122 each time that a measurement environment changes, and this operation may consume time and calculation resources.

Figure 12:
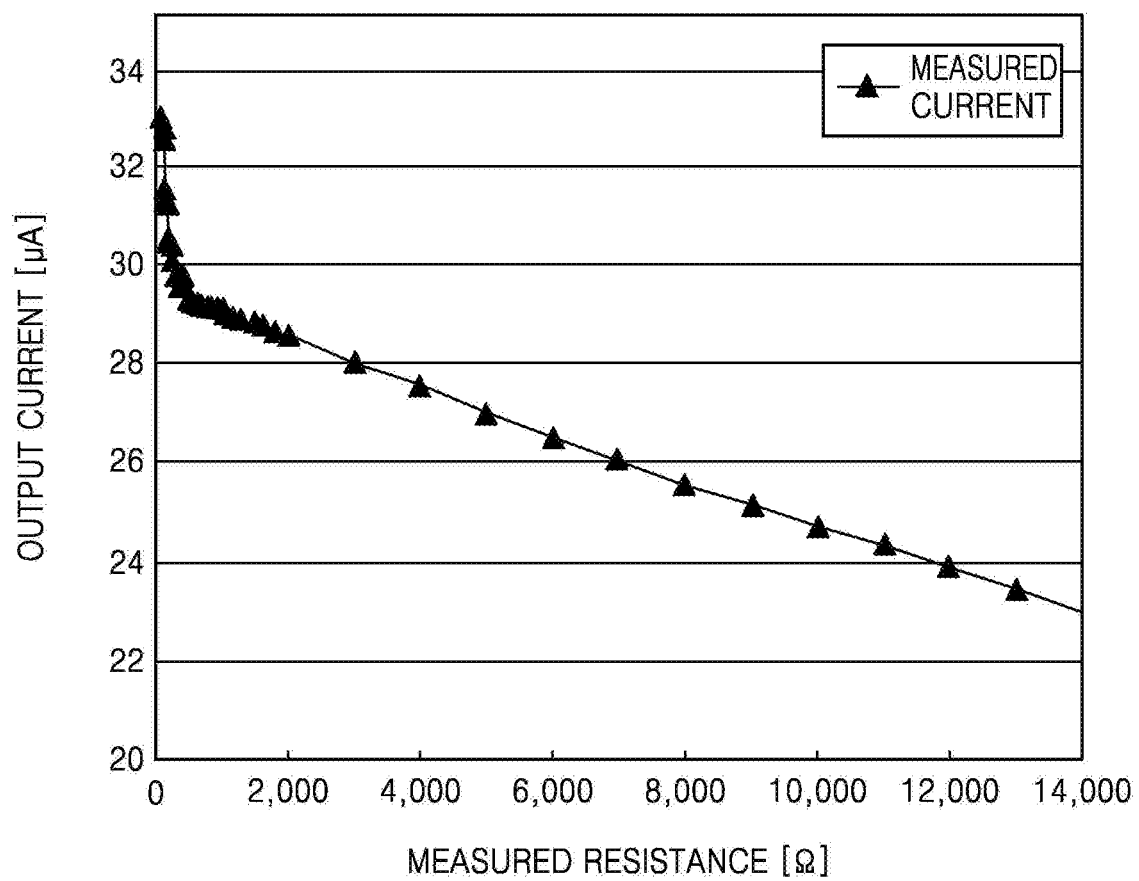
FIG. 12 is a graph illustrating a change of a current amount supplied to an electrode unit depending on a change of a first impedance value with a current source parallel impedance connected thereto.

FIG. 12 is a graph illustrating a change of a current amount supplied to the electrode unit 110 depending on a change of the first impedance value $Z_{4P}$ with a current source parallel impedance $Z_{SEXT}$ 127 connected.

In FIG. 12, a horizontal axis represents the magnitude of the first impedance value $Z_{4P}$ measured by the impedance measurer 120. A vertical axis represents a current $I_1$ (see FIG. 4) supplied to the electrode unit 110 from among a current output from the current source 122.

Referring to FIG. 12, it is shown that when the magnitude of the first impedance value $Z_{4P}$ increases, a graph of a change in the magnitude of the current supplied to the electrode unit 110 may be approximately a straight line. This result is because the effective value $Z_{SEFF}$ of the internal impedance Zs nearly does not change at all, and thus the current substantially depends on only the first impedance value $Z_{4P}$. Therefore, the bio impedance obtainer 140 may obtain the bio impedance value Zm without changing the effective value $Z_{SEFF}$ of the internal impedance Zs of the current source 122 even when a measurement environment changes. Also, since the graph of FIG. 12 represents a straight line, prediction of the current amount supplied to the electrode unit 110 may be easy.

FIGS. 4 to 12 describe an example in which contact impedances of the first to fourth electrodes 110a, 110b, 110c, and 110d are the same. However, depending on various criteria, such as user intentions, examinee characteristics, environmental characteristics, hardware factors, etc., the contact impedances of the first to fourth electrodes 110a, 110b, 110c, and 110d may not be the same.

Figure 13:
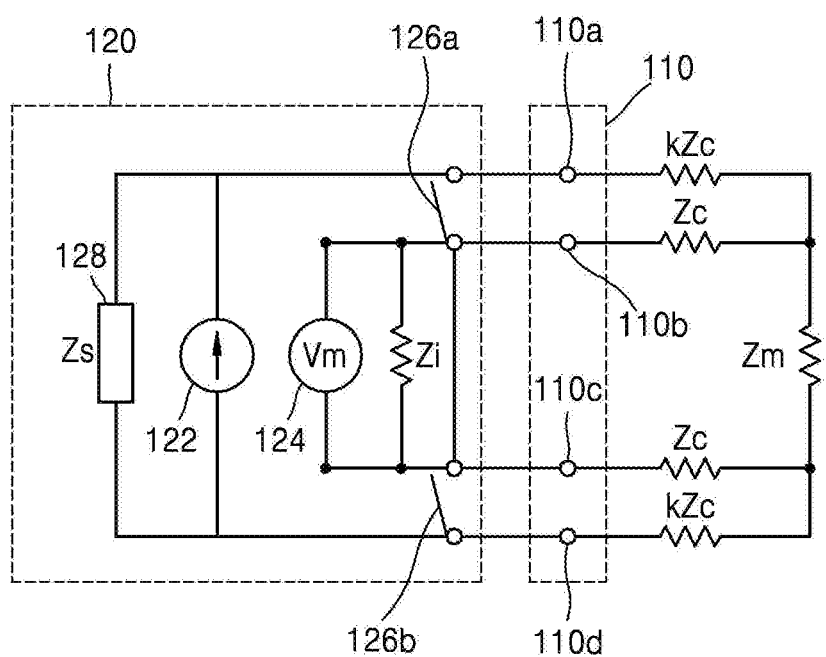
FIG. 13 is another circuit diagram for explaining an apparatus for measuring a bio signal according to an exemplary embodiment.

FIG. 13 is another circuit diagram for explaining an apparatus 100 for measuring a bio signal according to an exemplary embodiment.

Referring to FIG. 13, contact impedance with respect to an examinee may be different for respective electrodes 110a, 110b, 110c, and 110d. FIG. 13 illustrates the case where one contact impedance is represented as a multiple of another contact impedance. For example, in the case where the area of the first and fourth electrodes 110a and 110d are less than the area of the second and third electrodes 110b and 110c by 1/k times, the contact impedances of the second and third electrodes 110b and 110c may be represented by Zc, and the contact impedances of the first and fourth electrodes 110a and 110d may be represented by k×Zc.

Figure 14:
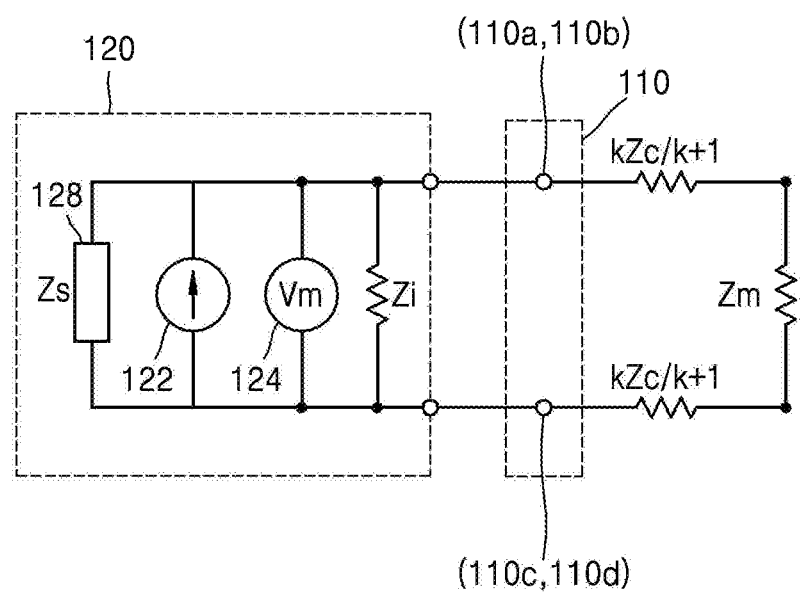
FIG. 14 is a circuit diagram for explaining a state in which an impedance measurer operates according to a second mode.

FIG. 14 is a circuit diagram for explaining a state in which the impedance measurer 120 is operating according to the second mode.

Referring to FIG. 14, the first and second switches 126a and 126b may be switched to a closed state, so that the first electrode 110a and the second electrode 110b may be short-circuited, and the third electrode 110c and the fourth electrode 110d may be short-circuited. When the first electrode 110a and the second electrode 110b are short-circuited, contact impedance k×Zc of the first electrode 110a and contact impedance Zc of the second electrode 110b are parallel-connected, so that a synthesized impedance value of kZc/(k+1) may be obtained. Also, when the third electrode 110c and the fourth electrode 110d are short-circuited, contact impedance Zc of the third electrode 110c and contact impedance k×Zc of the fourth electrode 110d are parallel-connected, so that a synthesized impedance value of kZc/(k+1) may be obtained.

The impedance measurer 120 may measure the first impedance value $Z_{4P}$ according to the first mode illustrated in FIG. 13, and measure the second impedance value $Z_{2P}$ according to the second mode illustrated in FIG. 14. Also, the bio impedance obtainer 140 may obtain the bio impedance Zm by compensating for a contact impedance effect of the electrodes 110a, 110b, 110c, and 110d by taking into account the first and second impedance values $Z_{4P}$ and $Z_{2P}$ and the internal impedance Zs of the current source 122. When the bio impedance obtainer 140 obtains the bio impedance Zm, Equation 9 may be used.

$$Z_m = Z_{4P} \frac{\left(\frac{k+1}{2a}\beta + Z_i\right)\left(\frac{k+1}{2}\beta + Z_S\right)}{Z_{4P}\left(\frac{(k+1)^2}{2k}\beta + kZ_i + \frac{Z_S}{k}\right) + Z_i Z_S} \quad \text{Equation 9}$$

In Equation 9, $\beta$ is defined by Equation 6. The bio impedance obtainer 140 may directly calculate the bio impedance Zm by using Equation 9 or obtain the bio impedance Zm by using the lookup table 146 or other information source which functions in a similar fashion as the lookup table 146.

In the above-described example, a multiple relation is established between contact impedances as a result of comparison of the cross-sectional areas of the electrodes 110a, 110b, 110c, and 110d. However, depending on the cases, a multiple relation may not be established.

Figure 15:
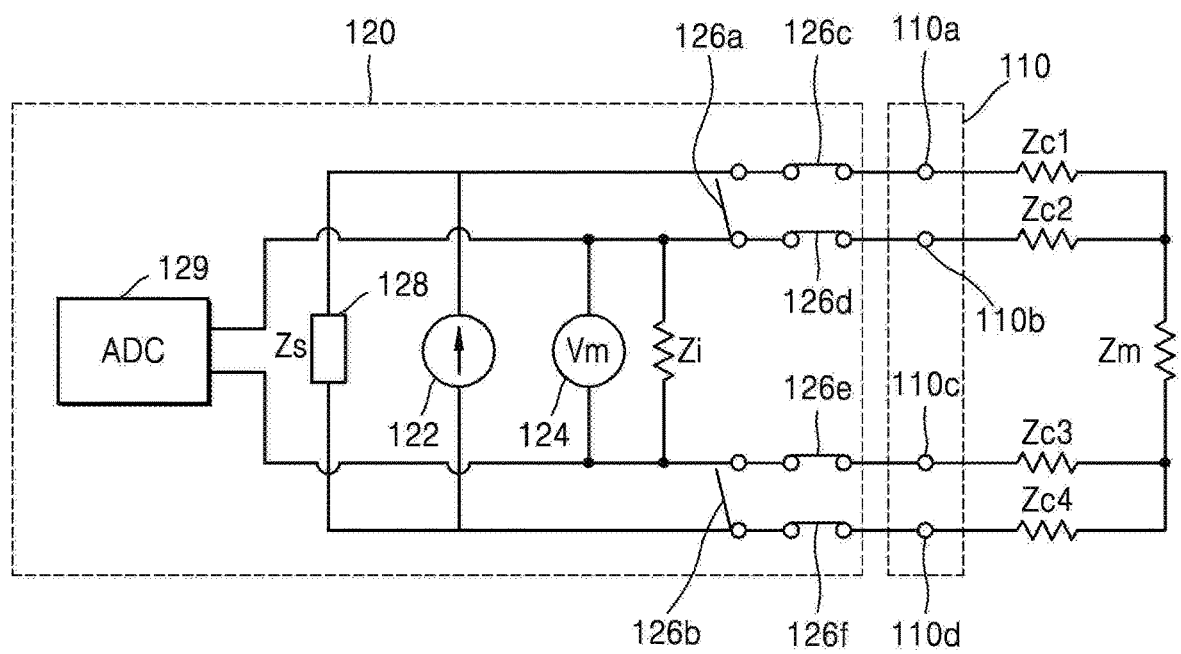
FIG. 15 is another circuit diagram for explaining an apparatus for measuring a bio signal according to an exemplary embodiment.

FIG. 15 is a circuit diagram for explaining an apparatus 100 for measuring a bio signal according to an exemplary embodiment.

Referring to FIG. 15, all contact impedances Zc1, Zc2, Zc3, and Zc4 of the first to fourth electrodes 110a, 110b, 110c, and 110d may have different values, respectively. Unlike FIG. 4, since all the contact impedances Zc1, Zc2, Zc3, and Zc4 have different values in the circuit diagram of FIG. 15, there are five unknowns Zm, Zc1, Zc2, Zc3, and Zc4 in total. Therefore, the mode controller 130 illustrated in FIG. 1 may control the impedance measurer 120 in five modes. The mode controller 130 may control the impedance measurer 120 under the first mode as illustrated in FIG. 15. Under the first mode, the current source 122 may be connected between the first electrode 110a and the fourth electrode 110d, and the voltmeter 124 may be connected between the second electrode 110b and the third electrode 110c. The first impedance Z1 measured under the first mode may be expressed by Equation 10.

$$Z_1 = Z_m \times \frac{1}{1 + \frac{Z_m + Z_{C2} + Z_{C3}}{Z_i}} \times \quad \text{Equation 10}$$

$$\frac{Z_S}{Z_S + Z_{C1} + Z_{C4} + \frac{1}{\frac{1}{Z_m} + \frac{1}{Z_{C2} + Z_{C3} + Z_i}}}$$

Figure 16:
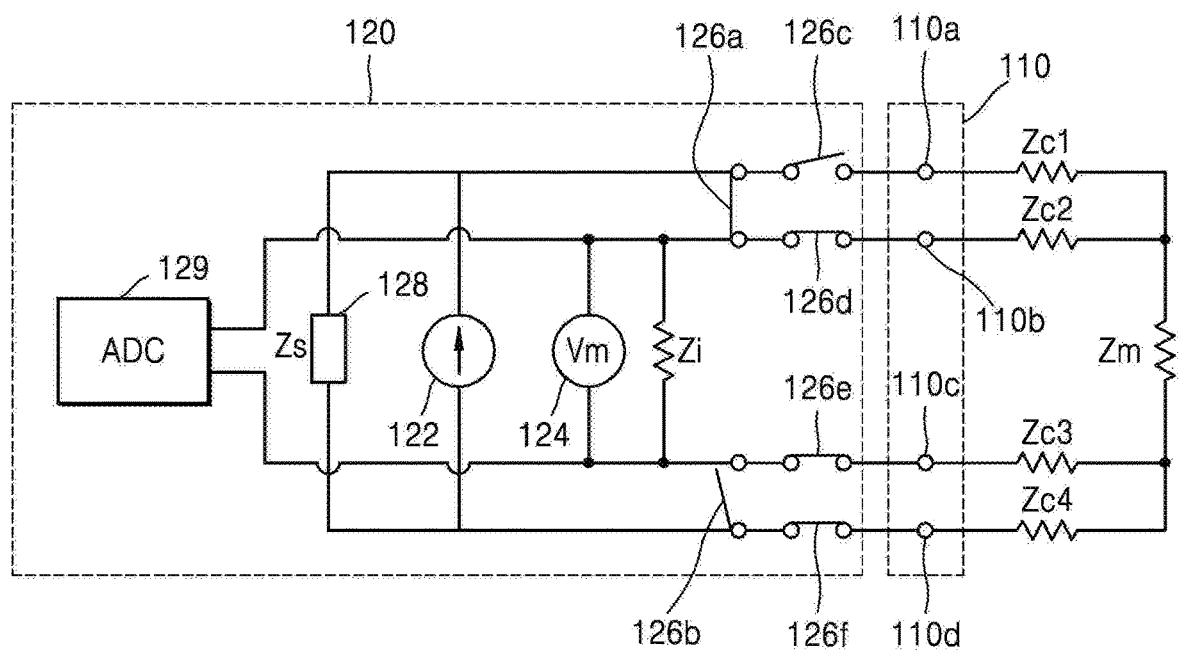
FIG. 16 is another circuit diagram for explaining a state in which an impedance measurer operates according to a second mode.

FIG. 16 is a circuit diagram for explaining a state in which an impedance measurer 120 is operating according to the second mode. The bio impedance Zm may be measured at a 2-point when operating according to the second mode illustrated in FIG. 14, or alternatively, the bio impedance Zm may be measured at a 3-point when operating according to the second mode illustrated in FIG. 16.

Referring to FIG. 16, according to the second mode, the current source 122 may be connected between the second electrode 110b and the fourth electrode 110d. The mode controller 130 may switch the first switch 126a to a closed state so that the current source 122 may be connected between the second electrode 110b and the fourth electrode 110d. Also, the voltmeter 124 may be connected between the second electrode 110b and the third electrode 110c. Also, the first electrode 110a may be electrically disconnected from the current source 122. The mode controller 130 may switch the third switch 126c to an open state so that the first electrode 110a may be electrically disconnected from the current source 122. When the first electrode 110a is electrically disconnected from the current source 122, a current may not flow through the first electrode 110a. When the current does not flow through the first electrode 110a, 3-point measurement may be performed according to the second mode. A second impedance value $Z_2$ measured according to the second mode may be expressed by Equation 11.

$$Z_2 = \frac{Z_{C2} + Z_m}{Z_i + Z_{C3} + Z_{C2} + Z_m} \times \quad \text{Equation 11}$$

$$\frac{Z_i}{Z_{C3} + Z_i} \times \frac{Z_S}{Z_S + Z_{C4} + \frac{1}{\frac{1}{Z_{C3} + Z_i} + \frac{1}{Z_{C2} + Z_m}}}$$

Figure 17:
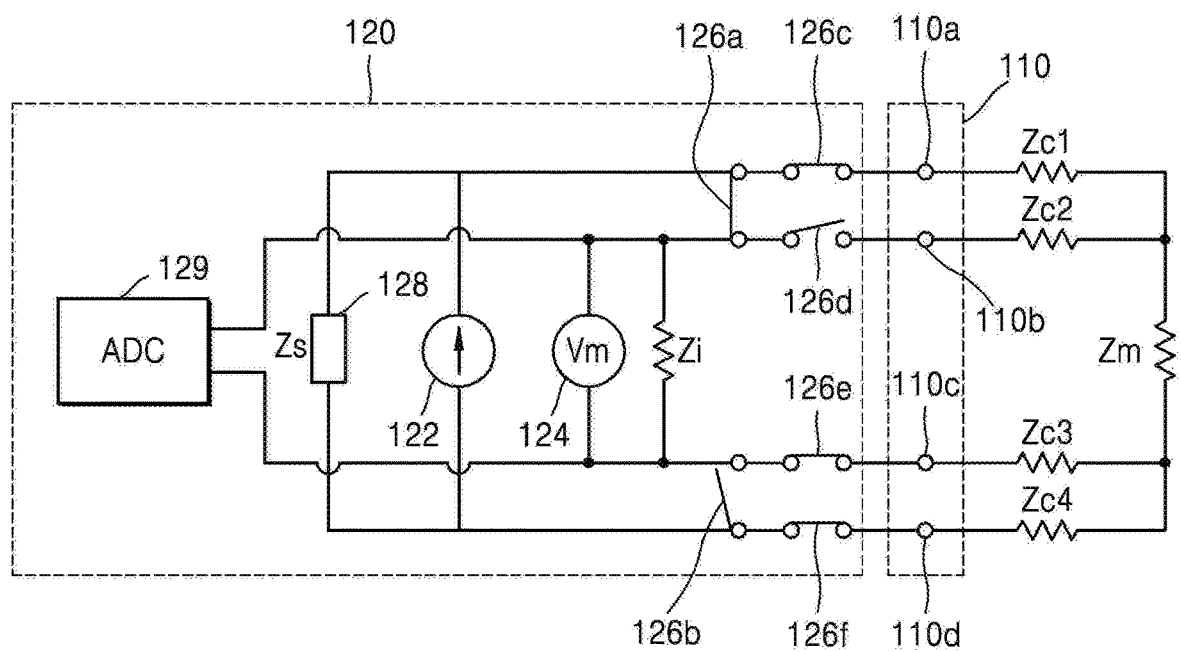
FIG. 17 is a circuit diagram for explaining a state in which an impedance measurer operates according to a third mode.

FIG. 17 is a circuit diagram for explaining a state in which an impedance measurer 120 operates according to a third mode.

Referring to FIG. 17, when operating according to the third mode, the current source 122 may be connected between the first electrode 110a and the fourth electrode 110d. Also, the voltmeter 124 may be connected between the first electrode 110a and the third electrode 110c. The mode controller 130 may switch the first switch 126a to a closed state so that the voltmeter 124 may be connected between the first electrode 110a and the third electrode 110c. Also, the second electrode 110b may be electrically disconnected from the current source 122. The mode controller 130 may switch the fourth switch 126d to an open state so that the second electrode 110b may be electrically disconnected from the current source 122. When the second electrode 110b is electrically disconnected from the current source 122, a current may not flow through the second electrode 110b. When the current does not flow through the second electrode 110b, a 3-point measurement may be performed according to the third mode. A third impedance value $Z_3$ measured according to the third mode may be expressed by Equation 12.

$$Z_3 = \frac{Z_{C1} + Z_m}{Z_i + Z_{C3} + Z_{C1} + Z_m} \times \quad \text{Equation 12}$$

$$\frac{Z_i}{Z_{C3} + Z_i} \times \frac{Z_S}{Z_S + Z_{C4} + \frac{1}{\frac{1}{Z_{C3} + Z_i} + \frac{1}{Z_{C1} + Z_m}}}$$

Figure 18:
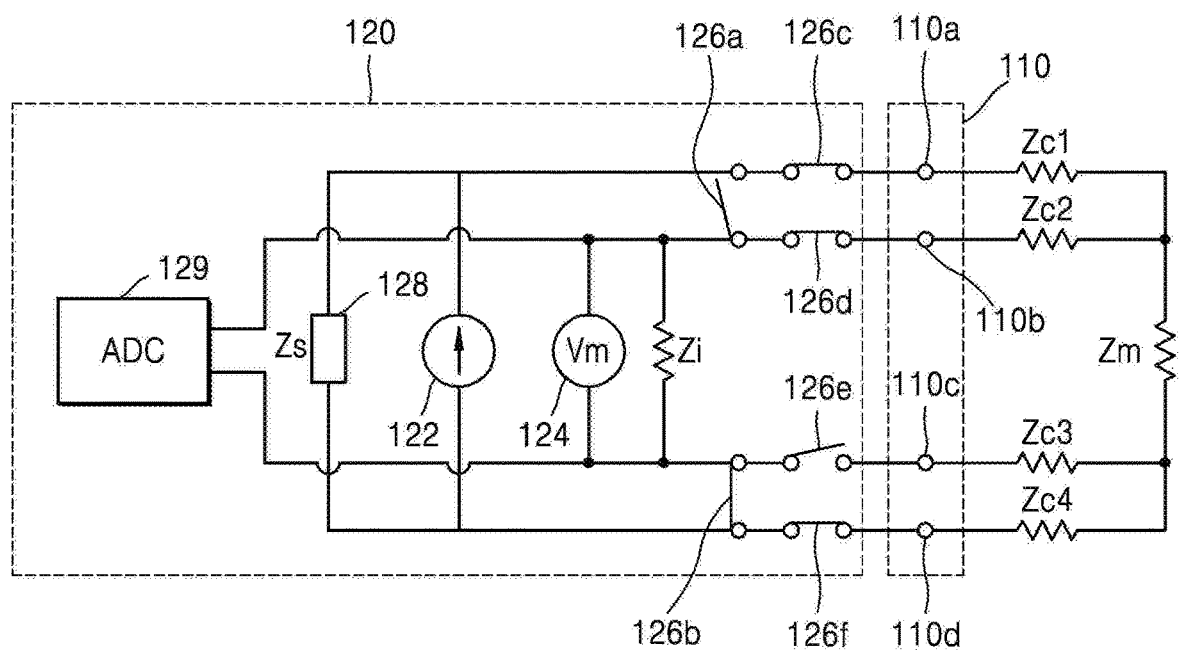
FIG. 18 is a circuit diagram for explaining a state in which an impedance measurer operates according to a fourth mode.

FIG. 18 is a circuit diagram for explaining a state in which an impedance measurer 120 operates according to a fourth mode.

Referring to FIG. 18, when operating according to the fourth mode, the current source 122 may be connected between the first electrode 110a and the fourth electrode 110d. Also, the voltmeter 124 may be connected between the second electrode 110b and the fourth electrode 110d. The mode controller 130 may switch the second switch 126b to a closed state so that the voltmeter 124 may be connected between the second electrode 110b and the fourth electrode 110d. Also, the third electrode 110c may be electrically disconnected from the current source 122. The mode controller 130 may switch a fifth switch 126e to an open state so that the third electrode 110c may be electrically disconnected from the current source 122. When the third electrode 110c is electrically disconnected from the current source 122, a current may not flow through the third electrode 110c. When the current does not flow through the third electrode 110c, a 3-point measurement may be performed according to the fourth mode. A fourth impedance value $Z_4$ measured according to the fourth mode may be expressed by Equation 13.

$$Z_3 = \frac{Z_{C4} + Z_m}{Z_i + Z_{C2} + Z_{C4} + Z_m} \times \frac{Z_i}{Z_{C2} + Z_i} \times \frac{Z_S}{Z_S + Z_{C1} + \cfrac{1}{\cfrac{1}{Z_{C2} + Z_i} + \cfrac{1}{Z_{C4} + Z_m}}} \quad \text{Equation 13}$$

Figure 19:
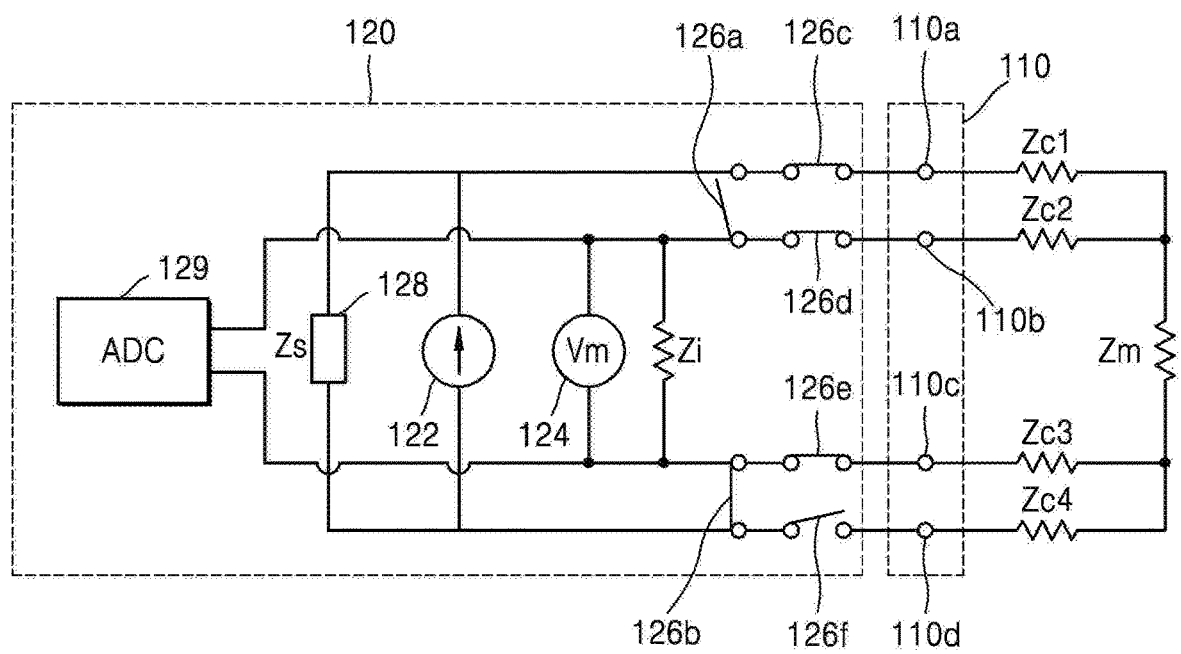
FIG. 19 is a circuit diagram for explaining a state in which an impedance measurer operates according to a fifth mode.

FIG. 19 is a circuit diagram for explaining a state in which an impedance measurer 120 operates according to a fifth mode.

Referring to FIG. 19, when operating according to the fifth mode, the current source 122 may be connected between the first electrode 110a and the third electrode 110c. The mode controller 130 may switch the second switch 126b to a closed state so that the current source 122 may be connected between the first electrode 110a and the third electrode 110c. Also, the voltmeter 124 may be connected between the second electrode 110b and the third electrode 110c. Also, the fourth electrode 110d may be electrically disconnected from the current source 122. The mode controller 130 may switch a sixth switch 126f to an open state so that the fourth electrode 110d may be electrically disconnected from the current source 122. When the fourth electrode 110d is electrically disconnected from the current source 122, a current may not flow through the fourth electrode 110d. When the current does not flow through the fourth electrode 110d, a 3-point measurement may be performed according to the fifth mode. A fifth impedance value $Z_5$ measured according to the fifth mode may be expressed by Equation 14.

$$Z_5 = \frac{Z_{C3} + Z_m}{Z_i + Z_{C2} + Z_{C3} + Z_m} \times \frac{Z_i}{Z_{C2} + Z_i} \times \frac{Z_S}{Z_S + Z_{C1} + \cfrac{1}{\cfrac{1}{Z_{C2} + Z_i} + \cfrac{1}{Z_{C3} + Z_m}}} \quad \text{Equation 14}$$

In the above, FIGS. 16 to 19 illustrate an example of making a 3-point measurement by electrically disconnecting one of the first to fourth electrodes 110a, 110b, 110c, and 110d from the current source 122. However, exemplary embodiments are not limited thereto. For example, a 3-point measurement may be made by separating one of the first to fourth electrodes 110a, 110b, 110c, and 110d from the examinee. Additionally, the exemplary embodiments are not limited to using four electrodes, and other numbers of electrodes (e.g., five, six, eight, etc.) may be used according to other exemplary embodiments. When four electrodes are used, exemplary embodiments may improve the accuracy of the four points probe method (also referred to as four terminal sensing or 4T sensing) by considering an internal impedance of the impedance measurer 120.

When the impedance measurer 120 measures the first to fifth impedance values $Z_1$, $Z_2$, $Z_3$, $Z_4$, and $Z_5$, the bio impedance obtainer 140 may obtain the bio impedance Zm by compensating for an effect of contact impedances Zc1, Zc2, Zc3, and Zc4 in the first to fifth impedance values $Z_1$, $Z_2$, $Z_3$, $Z_4$, and $Z_5$. The bio impedance obtainer 140 may take into account the internal impedance Zs of the current source 122 when compensating for the effect of the contact impedances Zc1, Zc2, Zc3, and Zc4. Exemplarily, the bio impedance Zm may be obtained by simultaneously solving Equations 10 to 14. In Equations 10 to 14, the first to fifth impedance values $Z_1$, $Z_2$, $Z_3$, $Z_4$, and $Z_5$ are measured values and Zi is a value determined depending on a characteristic of the AFE. Therefore, Zc1, Zc2, Zc3, Zc4, and Zm may be calculated by simultaneously solving Equations 10 to 14, and even when values of Zc1, Zc2, Zc3, and Zc4 are not known or not calculated, Zm may be calculated. The bio impedance obtainer 140 may directly calculate simultaneous Equations 10 to 14 in order to obtain the bio impedance Zm. As another example, the bio impedance obtainer 140 may obtain the bio impedance Zm by using the lookup table 146 illustrated in FIG. 8. The lookup table 146 may output the bio impedance value Zm from the first to fifth impedance values $Z_1$, $Z_2$, $Z_3$, $Z_4$, and $Z_5$ or voltage values Vm measured under the first to fifth modes.

Referring to FIG. 4 again, the exemplary embodiment illustrated in FIG. 4 changes the equations which the bio impedance obtainer 140 uses for obtaining the bio impedance Zm from Equations 1 and 2 to Equations 3 and 4 in order to compensate for a difference between the output current I of the current source 122 and the current $I_1$ supplied to the electrode unit 110. However, exemplary embodiments are not limited thereto. For example, the bio impedance obtainer 140 may not use the internal impedance Zs when obtaining the bio impedance Zm.

Figure 20:
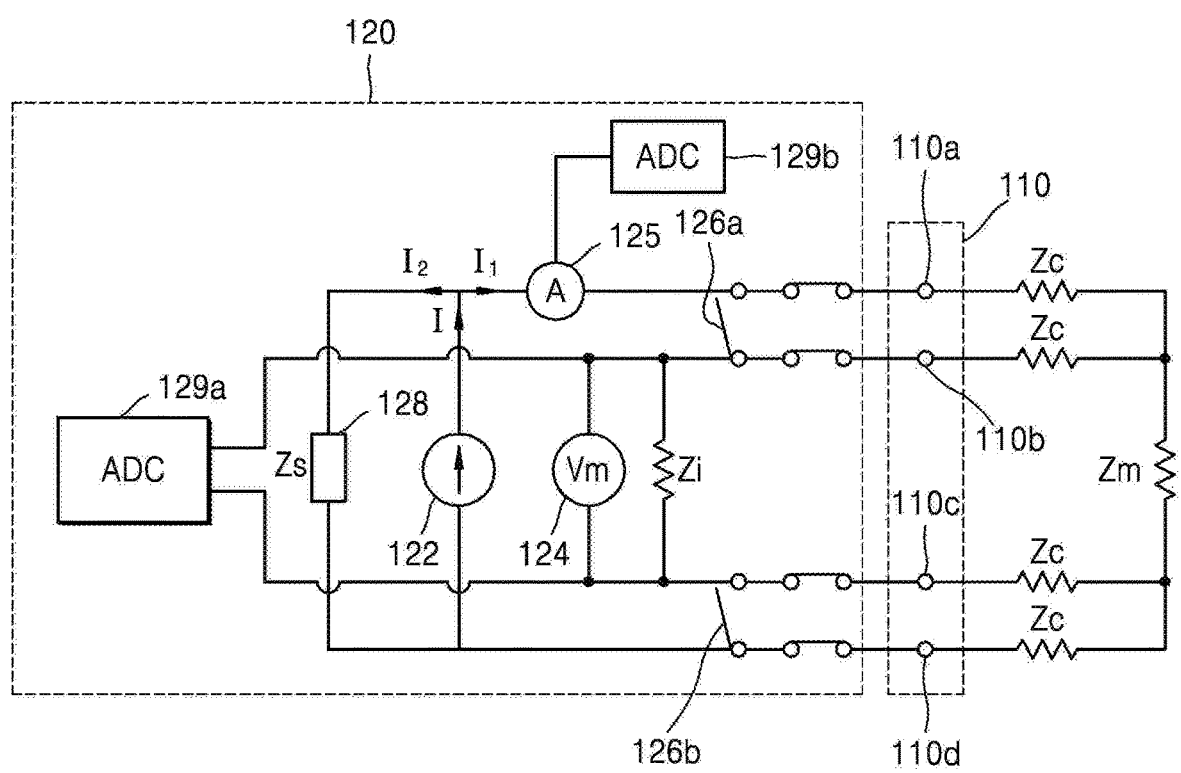
FIGS. 20 and 21 are circuit diagrams for explaining an apparatus for measuring a bio signal according to an exemplary embodiment.
Figure 21:
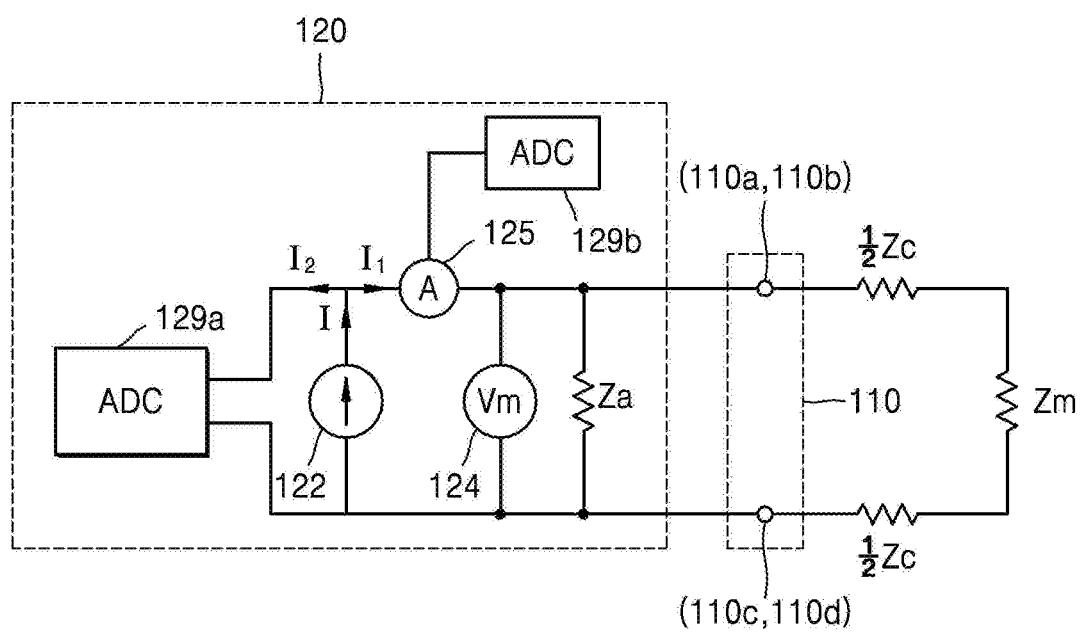

FIGS. 20 and 21 are circuit diagrams for explaining an apparatus 100 for measuring a bio signal according to an exemplary embodiment. FIG. 20 illustrates a state in which an impedance measurer 120 operates according to the first mode, and FIG. 21 illustrates a state in which the impedance measurer 120 operates according to the second mode.

Referring to FIGS. 20 and 21, the impedance measurer 120 may include an amperemeter 125 for measuring the current $I_1$ supplied to the electrode unit 110. The amperemeter 125 may be disposed between the current source 122 and the electrode unit 110. Also, a second ADC 129 for converting the magnitude of a measured current into a digital signal may be connected to the amperemeter 125. The first impedance value $Z_{4P}$ may be determined by dividing a voltage value Vm measured by the voltmeter 124 by a current value $I_1$ measured by the amperemeter 125.

In the above description of FIGS. 4 and 5, the first and second impedance values $Z_{4P}$ and $Z_{2P}$ are described as being determined by dividing a voltage Vm by an output current I of the current source 122. Therefore, Equations 3 and 4, which are equations used to calculate the first and second impedance values $Z_{4P}$ and $Z_{2P}$, include a factor that depends on the internal impedance Zs of the current source 122.

In contrast, in the exemplary embodiment illustrated in FIGS. 20 and 21, the first and second impedance values $Z_{4P}$ and $Z_{2P}$ may be determined by dividing a voltage Vm by a current $I_1$ measured by the amperemeter 125. In this case, the first and second impedance values $Z_{4P}$ and $Z_{2P}$ may be expressed by Equations 1 and 2. Equations 1 and 2 do not include a factor that depends on the internal impedance Zs of the current source 122. That is, the bio impedance obtainer 140 may obtain the bio impedance Zm by simultaneously solving Equations 1 and 2 even without using the internal impedance Zs of the current source 122.

Figure 22:
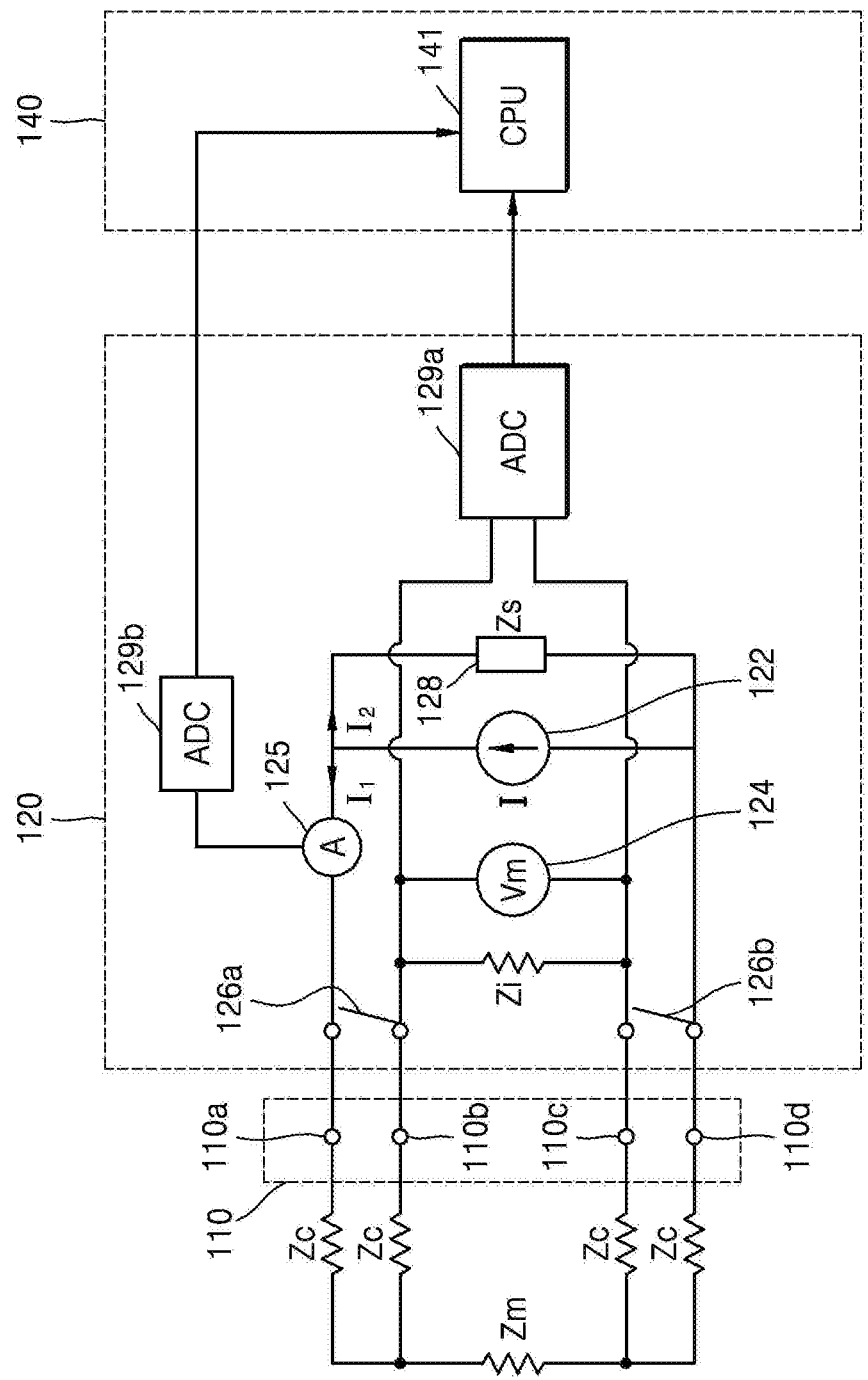
FIG. 22 is another circuit diagram for explaining an apparatus for measuring a bio signal according to an exemplary embodiment.

FIG. 22 is another circuit diagram for explaining an apparatus 100 for measuring a bio signal according to an exemplary embodiment.

Referring to FIG. 22, a first ADC 129a of the impedance measurer 120 may convert the magnitude of a voltage measured by the voltmeter 124 into a digital signal and transfer the digital signal to a CPU 141 of the bio impedance obtainer 140. Also, a second ADC 129b may convert the magnitude of a current measured by the amperemeter 125 into a digital signal and transfer the digital signal to the CPU 141 of the bio impedance obtainer 140. The CPU 141 may calculate the first and second impedance values $Z_{4P}$ and $Z_{2P}$ from input voltage value and current value. The CPU 141 may calculate the bio impedance Zm by solving simultaneous Equations 1 and 2.

For another example, the bio impedance obtainer 140 may obtain the bio impedance Zm by using a lookup table instead of directly calculating the bio impedance Zm.

Figure 23:
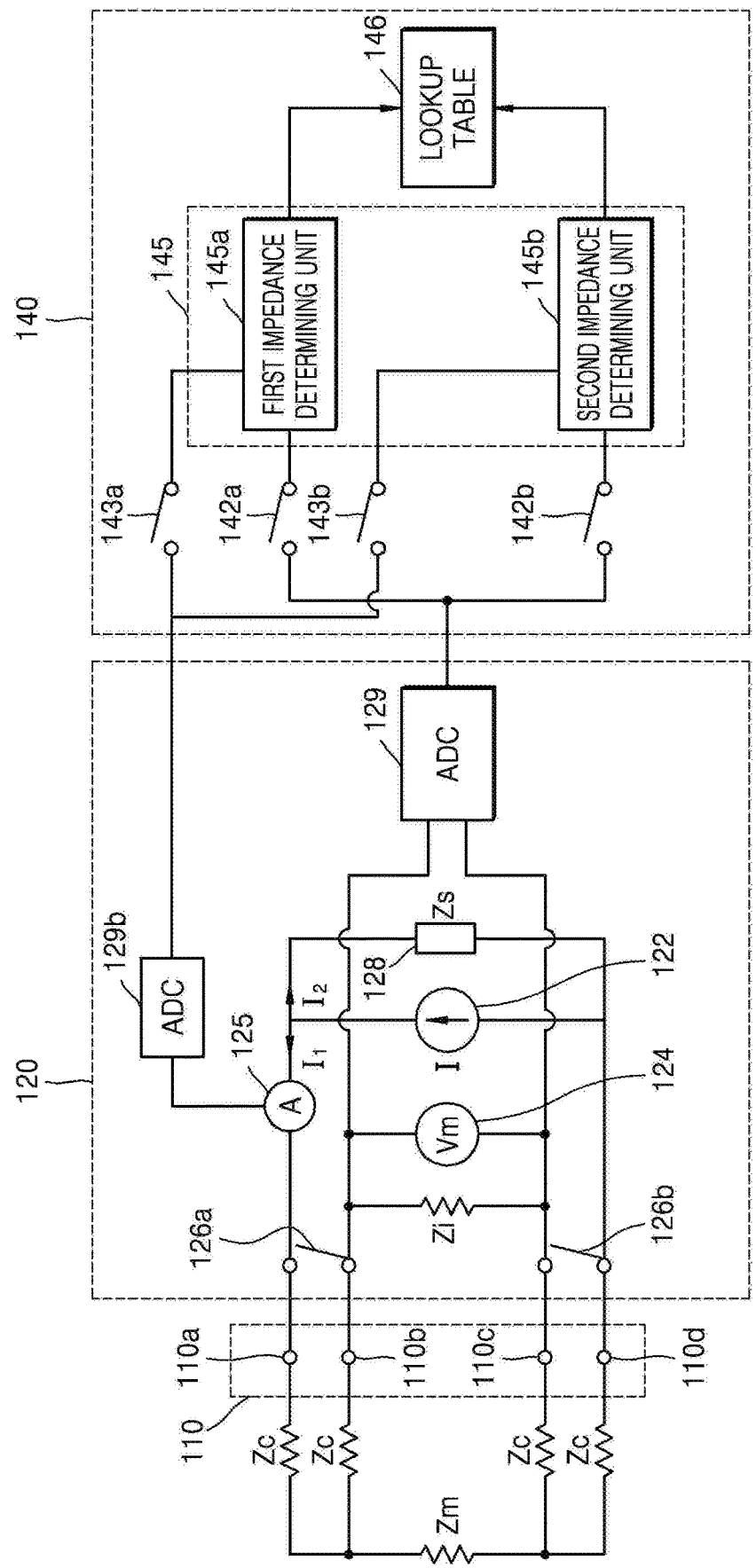
FIG. 23 is another circuit diagram for explaining an apparatus for measuring a bio signal according to an exemplary embodiment.

FIG. 23 is another circuit diagram for explaining an apparatus 100 for measuring a bio signal according to an exemplary embodiment.

Referring to FIG. 23, the bio impedance obtainer 140 may include an impedance determiner 145. The impedance determiner 145 may determine the first and second impedance values $Z_{4P}$ and $Z_{2P}$ by receiving information regarding measured voltage and current from the impedance measurer 120. Exemplarily, the impedance determiner 145 may include a first impedance determining unit (e.g., first impedance determiner) 145a and a second impedance determining unit (e.g., second impedance determiner) 145b.

The first ADC 129a may convert the magnitude of a voltage measured by the voltmeter 124 into a digital signal. The second ADC 129b may convert the magnitude of a current measured by the amperemeter 125 into a digital signal. Connections between the first and second ADCs 129a and 129b, and the first and second impedance determiners 145a and 145b, may change depending on a connection state of switches 142a, 142b, 143a, and 143b.

For example, while the impedance measurer 120 is operating according to the first mode, the upper switches 142a and 143a may be closed, and the lower switches 142b and 143b may be open. The first impedance determiner 145a may receive voltage and current values measured according to the first mode and determine the first impedance value $Z_{4P}$.

While the impedance measurer 120 is operating according to the second mode, the upper switches 142a and 143a may be open, and the lower switches 142b and 143b may be closed. The second impedance determiner 145b may receive voltage and current values measured according to the second mode and determine the second impedance value $Z_{2P}$.

The lookup table 146 may receive first and second impedance values $Z_{4P}$ and $Z_{2P}$ determined by the first and second impedance measurers 145a and 145b and output bio impedance Zm.

In the above, the method of obtaining the bio impedance Zm of the examinee at the apparatus 100 for measuring a bio signal has been described. The apparatus 100 for measuring a bio signal may output bio information of the examinee based on the bio impedance Zm.

Figure 24:
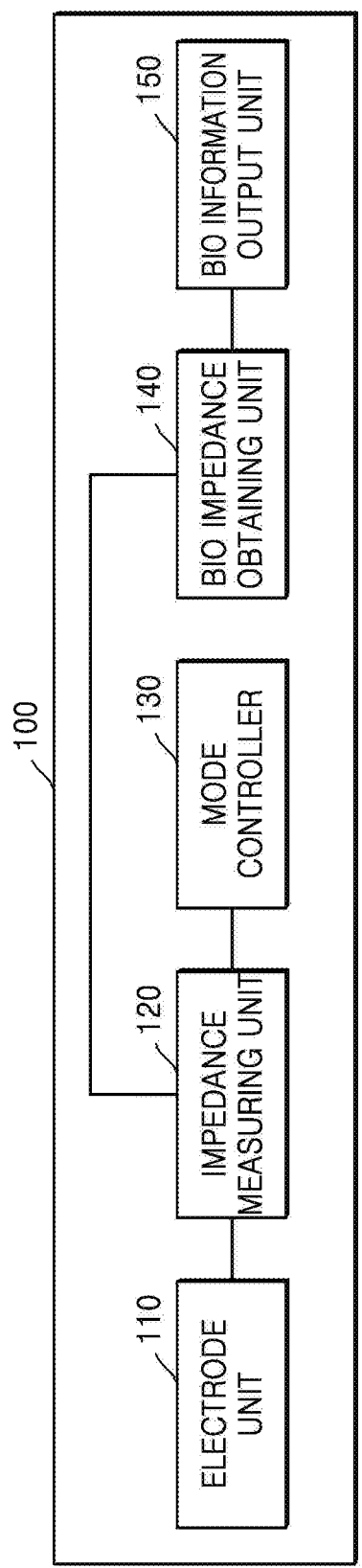
FIG. 24 is another block diagram for explaining an apparatus for measuring a bio signal according to an exemplary embodiment.

FIG. 24 is a block diagram for explaining an apparatus 100 for measuring a bio signal according to an exemplary embodiment.

Referring to FIG. 24, the apparatus 100 for measuring a bio signal may further include a bio information output unit 150 (e.g., bio information outputter) for outputting bio information of an examinee from bio impedance Zm. The bio information output member 150 may output the bio information such as a body fat amount, a basal metabolic amount, a skeletal muscle amount, a blood flow amount, breathing, a heart rate, and heart rate variation of the examinee. Exemplarily, the bio information output member 150 may output the bio information of the examinee by using body information of the examinee and the bio impedance Zm obtained by the bio impedance obtainer 140. Here, the body information of the examinee may include information indicating many different characteristics of the examinee, e.g, an age, height, weight, etc., of the examinee.

Figure 25:
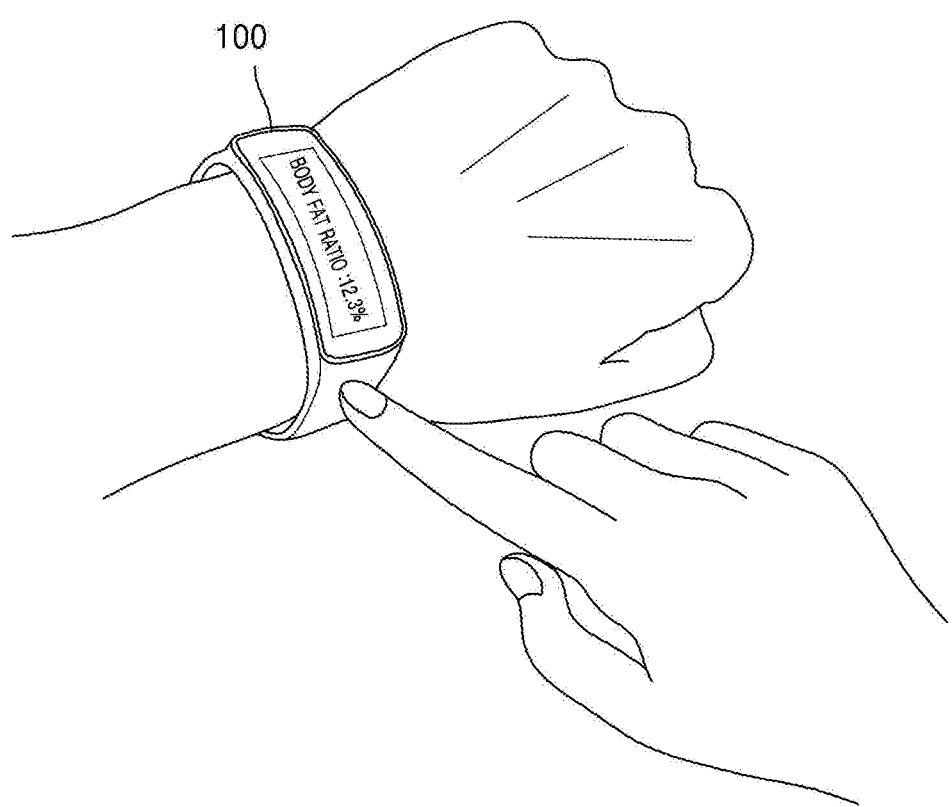
FIGS. 25 and 26 are perspective views illustrating an implementation of an apparatus for measuring a bio signal.
Figure 26:
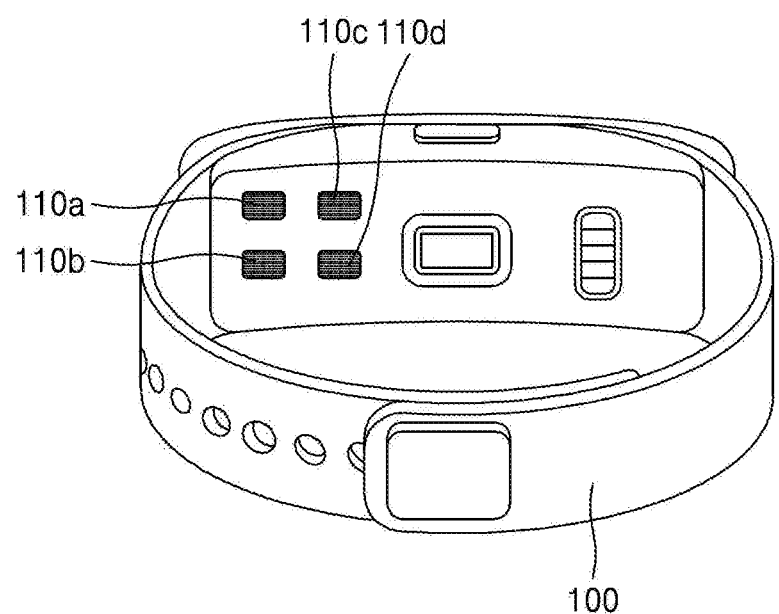

FIGS. 25 and 26 are perspective views illustrating an implementation of an apparatus 100 for measuring a bio signal.

Referring to FIGS. 25 and 26, the apparatus 100 for measuring a bio signal may be implemented in the form of a wearable apparatus such as a smart watch wearable on a wrist, a smart ring wearable on a finger, or many other types of smart devices which may or may not be wearable by a user, e.g., smart jewelry, smart shoes, headware, glasses, etc. In the case of a 2-point measurement method, the electrodes 110a, 110b, 110c, and 110d may be located inside the apparatus 100 for measuring a bio signal. When a user wears the apparatus 100 for measuring a bio signal on his wrist, the electrodes 110a, 110b, 110c, and 110d may contact the skin of a wrist portion.

Figure 27:
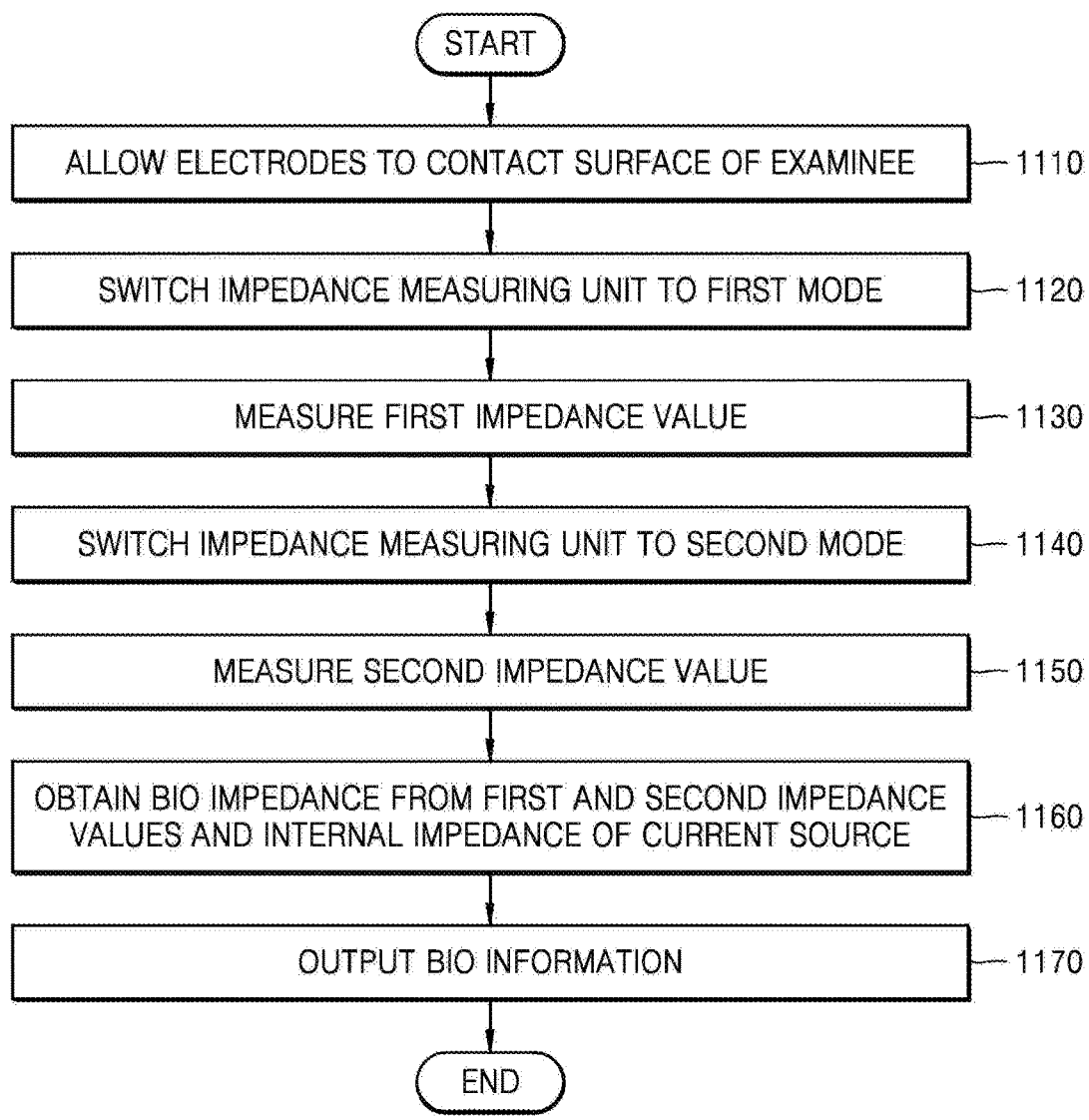
FIG. 27 is a flowchart illustrating a method of measuring a bio signal according to an exemplary embodiment.

FIG. 27 is a flowchart illustrating a method of measuring a bio signal according to an exemplary embodiment.

Referring to FIG. 27, the apparatus 100 for measuring a bio signal may measure the first and second impedance values $Z_{4P}$ and $Z_{2P}$ while changing a measurement mode of the impedance measurer 120. Also, the apparatus 100 for measuring a bio signal may obtain bio impedance Zm of the examinee from the first and second impedance values $Z_{4P}$ and $Z_{2P}$ and the internal impedance Zs of the current source 122. Also, the apparatus 100 for measuring a bio signal may output bio information of the examinee based on the obtained bio impedance Zm.

In operation S1110, the electrodes 110a, 110b, 110c, and 110d of the electrode unit 110 may be positioned to contact a surface (e.g., skin) of the examinee. All of the electrodes 110a, 110b, 110c, and 110d may contact the surface of the examinee, or alternatively, only a portion of the electrodes 110a, 110b, 110c, and 110d may contact the surface of the examinee.

In operation 1120, the mode controller 130 may switch the impedance measurer 120 to the first mode. Exemplarily, according to the first mode, the impedance measurer 120 may be switched to a state illustrated in FIG. 4. The mode controller 130 may control the switches 126a and 126b of the impedance measurer 120 in order to control the mode of the impedance measurer 120.

In operation 1130, the impedance measurer 120 may measure the first impedance value $Z_{4P}$. Exemplarily, as illustrated in FIG. 4, the impedance measurer 120 may measure the first impedance value $Z_{4P}$ by measuring a voltage Vm between the electrodes 110c and 110d by using the voltmeter 124.

In operation 1140, the mode controller 130 may switch the impedance measurer 120 to the second mode. Exemplarily, when operating according to the second mode, the impedance measurer 120 may be switched to a state illustrated in FIG. 5. However, this configuration shown in FIG. 5 is only exemplary and exemplary embodiments are not limited thereto. The configuration of the circuits according to the second mode may be an configuration which enables the impedance measurer 120 to measure an impedance value different from the impedance value of the first mode. Therefore, the impedance measurer 120 may be switched to a state different from the state illustrated in FIG. 5.

In operation 1150, the impedance measurer 120 may measure the second impedance value $Z_{2P}$. Exemplarily, as illustrated in FIG. 5, the impedance measurer 120 may measure the second impedance value $Z_{2P}$ by measuring a voltage Vm between the electrodes 110c and 110d by using the voltmeter 124.

In operation 1160, the bio impedance obtainer 140 may obtain bio impedance Zm from the first and second impedance values $Z_{4P}$ and $Z_{2P}$ and the internal impedance Zs of the current source 122. Since, when obtaining the bio impedance Zm, the bio impedance obtainer 140 takes into account the internal impedance Zs of the current source 122, the accuracy of the obtained bio impedance Zm may be improved.

In operation 1170, the bio information output member 150 may output bio information of the examinee from the bio impedance Zm. The bio information of the examinee output by the bio information output member 150 may include many different indicators of physical characteristics of the examinee, such as a body fat amount, a basal metabolic amount, a skeletal muscle amount, a blood flow amount, a breathing rate, a heart rate, heart rate variation, etc., of the examinee. The bio information output member 150 may output the bio information of the examinee via a display unit as illustrated in FIG. 25.

FIG. 27 illustrates an example in which the impedance measurer 120 measures the first and second impedance values $Z_{4P}$ and $Z_{2P}$ under two modes. However, a number of modes according to which the impedance measurer 120 measures impedance may be more than two. For example, as illustrated in FIG. 15, in the case where all of the contact impedances Zc1, Zc2, Zc3, and Zc4 of the electrodes 110a, 110b, 110c, and 110d are different from each other, the mode controller 130 may control the impedance measurer 120 using more than two modes.

Figure 28:
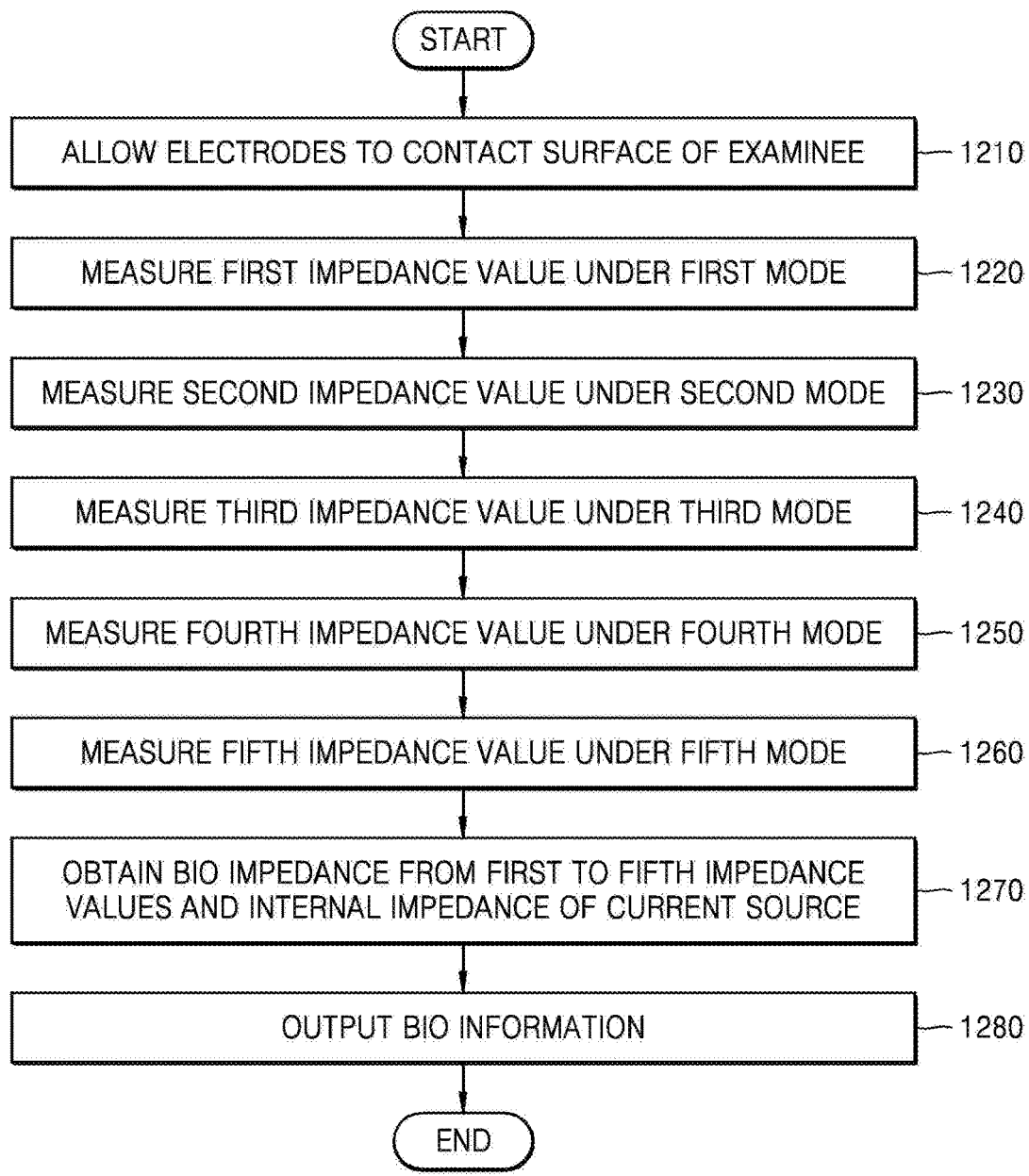
FIG. 28 is a flowchart illustrating a method of measuring a bio signal according to an exemplary embodiment.

FIG. 28 is a flowchart illustrating a method of measuring a bio signal according to an exemplary embodiment.

Referring to FIG. 28, the method of measuring a bio signal may measure the first to fifth impedance values $Z_1$, $Z_2$, $Z_3$, $Z_4$, and $Z_5$ while changing a measurement mode of the impedance measurer 120.

In operation 1220, the mode controller 130 may switch the impedance measurer 120 to the first mode as illustrated in FIG. 15. Also, the impedance measurer 120 may measure the first impedance value $Z_1$ under the first mode. The impedance measurer 120 may measure the first impedance value $Z_1$ by measuring a voltage by using the voltmeter 124.

In operation 1230, the mode controller 130 may switch the impedance measurer 120 to the second mode as illustrated in FIG. 16. Also, the impedance measurer 120 may measure the second impedance value $Z_2$ while operating according to the second mode. According to the second mode, a 3-point measurement may be performed with the first electrode 110a not being used for impedance measurement.

In operation 1240, the mode controller 130 may switch the impedance measurer 120 to the third mode as illustrated in FIG. 17. Also, the impedance measurer 120 may measure the third impedance value $Z_3$ according to the third mode. According to the third mode, a 3-point measurement may be performed with the second electrode 110b not being used for impedance measurement.

In operation 1250, the mode controller 130 may switch the impedance measurer 120 to the fourth mode as illustrated in FIG. 18. Also, the impedance measurer 120 may measure the fourth impedance value $Z_4$ according to the fourth mode. According to the fourth mode, a 3-point measurement may be performed with the third electrode 110c not being used for impedance measurement.

In operation 1260, the mode controller 130 may switch the impedance measurer 120 to the fifth mode as illustrated in FIG. 19. Also, the impedance measurer 120 may measure the fifth impedance value $Z_5$ according to the fifth mode. According to the fifth mode, a 3-point measurement may be performed with the fourth electrode 110d not being used for impedance measurement.

In operation 1270, the bio impedance obtainer 140 may obtain the bio impedance Zm from the first to fifth impedance values $Z_1$, $Z_2$, $Z_3$, $Z_4$, and $Z_5$ and the internal impedance Zs of the current source 122. The bio impedance obtainer 140 may calculate Zc1, Zc2, Zc3, Zc4, and Zm by simultaneously solving Equations 10 to 14, and even when values of Zc1, Zc2, Zc3, and Zc4 are not known or not calculated, the bio impedance obtainer 140 may calculate Zm. Also, the bio impedance obtainer 140 may output the bio impedance value Zm by using a lookup table instead of directly calculating the bio impedance value Zm.

Figure 29:
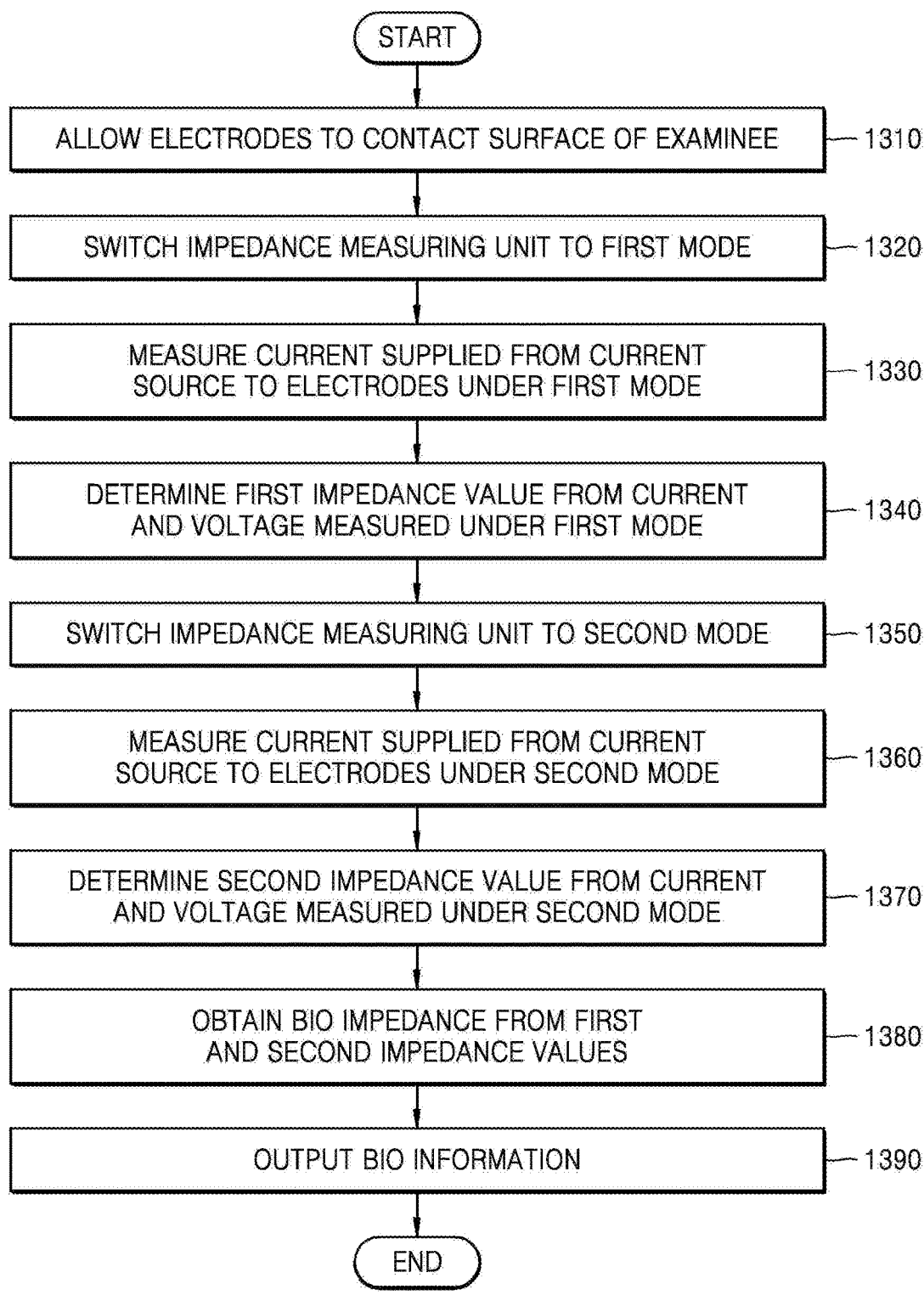
FIG. 29 is a flowchart illustrating a method of measuring a bio signal according to an exemplary embodiment.

FIG. 29 is a flowchart illustrating a method of measuring a bio signal according to an exemplary embodiment.

Referring to FIG. 29, the impedance measurer 120 may measure not only a voltage between the electrodes 110b and 110c but also a current amount supplied to the electrode unit 110 under each mode. Also, the first and second impedance values $Z_{4P}$ and $Z_{2P}$ may be determined by taking into account not only a voltage Vm measured by the voltmeter 124 but also a current $I_2$ measured by the amperemeter 125 according to each mode.

Hereinafter, respective operations of FIG. 29 are described with reference to FIGS. 20 to 23.

In operation 1310, the electrodes are positioned to contact a surface of the examinee.

In operation 1320, the mode controller 130 may switch the impedance measurer 120 to the first mode as illustrated in FIG. 20.

In operation 1330, the amperemeter 125 of the impedance measurer 120 may measure a current amount $I_1$ supplied to the electrode unit 110. The amperemeter 125 may measure the current amount $I_1$, thereby reflecting a change of the current amount $I_1$ supplied to the electrode unit 110 due to the internal impedance Zs of the current source 122 while obtaining the bio impedance Zm.

In operation 1340, the bio impedance obtainer 140 may determine the first impedance value $Z_{4P}$ from a voltage Vm and the current $I_1$ measured according to the first mode. The bio impedance obtainer 140 may determine the first impedance value $Z_{4P}$ by using the CPU 141 as illustrated in FIG. 22. As illustrated in FIG. 23, the bio impedance obtainer 140 may include the first impedance determiner 145a that determines the first impedance value $Z_{4P}$.

In operation 1350, the mode controller 130 switches the impedance measurer 120 to the second mode as illustrated in FIG. 21.

In operation 1360, the amperemeter 125 of the impedance measurer 120 may measure a current amount $I_1$ supplied to the electrode unit 110. The amperemeter 125 may measure the current amount $I_1$, thereby reflecting a change of the current amount $I_1$ supplied to the electrode unit 110 due to the internal impedance Zs of the current source 122 while obtaining the bio impedance Zm.

In operation 1370, the bio impedance obtainer 140 may determine the second impedance value $Z_{2P}$ from a voltage Vm and the current $I_1$ measured according to the second mode. The bio impedance obtainer 140 may determine the second impedance value $Z_{2P}$ by using the CPU 141 as illustrated in FIG. 22. As illustrated in FIG. 23, the bio impedance obtainer 140 may include the second impedance determiner 145b that determines the second impedance value $Z_{2P}$.

In operation 1380, the bio impedance obtainer 140 may obtain the bio impedance Zm from the first and second impedance values $Z_{4P}$ and $Z_{2P}$. In this case, the bio impedance Zm may be obtained from a result obtained by simultaneously solving Equations 1 and 2. Since a current change by the internal impedance Zs of the current source 122 has already been taken into account in the process of determining the first and second impedance values $Z_{4P}$ and $Z_{2P}$, the bio impedance obtainer 140 may obtain the bio impedance Zm even without using the internal impedance value Zs.

In the above description, the apparatus and method of measuring a bio signal according to the exemplary embodiments have been described with reference to FIGS. 1 to 29.

The apparatus for measuring a bio signal according to the exemplary embodiments may measure the bio impedance regardless of contact impedance.

Also, the apparatus for measuring a bio signal according to the exemplary embodiments may measure the bio impedance by using an electrode having a small size.

Also, the apparatus for measuring a bio signal according to the exemplary embodiments may improve the accuracy of a bio impedance measurement value by taking into account the internal impedance of the current source.

The apparatus according to the present exemplary embodiments may include a processor, a memory for storing program data and executing the stored program data, a permanent storage unit such as a disk drive, a communications port for handling communications with external devices, and user interface devices, including a touch panel, keys, buttons, etc. When software modules or algorithms are involved, these software modules may be stored as program instructions or computer-readable codes executable on a processor on a non-transitory computer-readable recording medium. Examples of the computer-readable recording medium include magnetic storage media (e.g., ROM, RAM, floppy disks, hard disks, etc.), and optical recording media (e.g., CD-ROMs, digital versatile disks (DVDs), etc.). The non-transitory computer-readable recording medium can also be distributed over network coupled computer systems so that the computer-readable code is stored and executed in a distributive manner. This media can be read by the computer, stored in the memory, and executed by the processor.

The exemplary embodiments may be described in terms of functional block components and various processing steps. Such functional blocks may be realized by any number of hardware and/or software components configured to perform the specified functions. For example, the exemplary embodiments may employ various integrated circuit (IC) components, e.g., memory elements, processing elements, logic elements, look-up tables, and the like, which may carry out a variety of functions under the control of one or more microprocessors or other control devices. Similarly, where the elements of the inventive concept are implemented using software programming or software elements, the exemplary embodiments may be implemented with any programming or scripting language such as C, C++, Java, assembler language, or the like, with the various algorithms being implemented with any combination of data structures, objects, processes, routines or other programming elements. Functional aspects may be implemented in algorithms that are executed on one or more processors. Furthermore, the exemplary embodiments could employ any number of techniques for electronics configuration, signal processing and/or control, data processing and the like. The words "mechanism," "element," "means," and "configuration" are used broadly and are not limited to mechanical or physical exemplary embodiments, but can include software routines in conjunction with processors, etc.

The particular implementations shown and described herein are illustrative examples of the exemplary embodiments and are not intended to otherwise limit the scope of the exemplary embodiments in any way. For the sake of brevity, electronics, control systems, software development and other functional aspects of the systems may not be described in detail. Furthermore, the connecting lines, or connectors, shown in the various figures are intended to represent exemplary functional relationships and/or physical or logical couplings between the various elements. It should be noted that many alternative or additional functional relationships, physical connections or logical connections may be present in an implemented device according to the exemplary embodiments.

The use of the terms "a" and "an" and "the" and similar referents in the context of describing the exemplary embodiments (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The exemplary embodiments are not limited to the described order of the steps. The use of any and all examples, or exemplary language (e.g., "such as") provided herein, is intended merely to better illuminate the exemplary embodiments and does not pose a limitation on the scope of the exemplary embodiments unless otherwise claimed. Numerous modifications and adaptations will be readily apparent to one of ordinary skill in the art without departing from the spirit and scope of the exemplary embodiments.

What is claimed is:

1. A method of measuring a bio signal using a bio signal measuring apparatus, an impedance measuring circuit of the bio signal measuring apparatus comprising a voltmeter, a current source, a plurality of electrodes comprising a pair of a first current electrode and a second current electrode to which the current source applies current, a pair of a first voltage electrode; and a second voltage electrode from which the voltmeter detects a voltage between the first voltage electrode and the second voltage electrode, a first switch disposed between the first current electrode and the first voltage electrode, and a second switch disposed between the second current electrode and the second voltage electrode, the method comprising:

positioning the plurality of electrodes to contact a surface of an examinee;
  measuring a first impedance value of the examinee while operating the impedance measuring circuit according to a first mode in which the first switch and the second switch are in an open state;
  measuring a second impedance value of the examinee while operating the impedance measuring circuit according to a second mode in which the first switch and the second switch are in a closed state; and
  obtaining bio impedance of the examinee by directly using the first impedance value, the second impedance value, an internal impedance value of the current source, and an input impedance value of the impedance measuring circuit as data for obtaining the bio impedance,
  wherein, in the second mode, an internal impedance of the current source, an input impedance of the impedance measuring circuit, the current source and the voltmeter are parallel-connected to each other, one end of each of the internal impedance of the current source, the input impedance of the impedance measuring circuit, the current source and the voltmeter is electrically connected to both the first current electrode and the first voltage electrode connected in parallel, and the other end of each of the internal impedance of the current source, the input impedance of the impedance measuring circuit, the electrically current source and the voltmeter is connected to both the second current electrode and the second voltage electrode connected in parallel.

2. The method of claim 1, wherein the measuring the first impedance value comprises measuring the first impedance value when the current source is connected between the first current electrode and the second current electrode, and the voltmeter is connected between the first voltage electrode and the second voltage electrode, according to the first mode.

3. The method of claim 2, wherein the measuring the second impedance value comprises measuring the second impedance value when a first common terminal of the current source and the voltmeter is connected to the first current electrode and the first voltage electrode, and a second common terminal of the current source and the voltmeter is connected to the second current electrode and the second voltage electrode, according to the second mode.

4. The method of claim 1, wherein the obtaining of the bio impedance of the examinee comprises:

obtaining the bio impedance of the examinee by compensating for an effect of contact impedance between the plurality of electrodes and the examinee in the first and second impedance values based on the internal impedance of the current source.

5. The method of claim 4, wherein the obtaining of the bio impedance of the examinee comprises:

obtaining the bio impedance of the examinee by using Equation 1:

$$Z_m = Z_{4P} = \frac{(\beta + Z_i)(\beta + Z_S)}{Z_{4P}(2\beta + Z_i + Z_S) + Z_i Z_S} \quad \text{Equation 1}$$

where $\beta$ is defined by Equation 2, $$\beta = \frac{2}{\frac{1}{Z_{2P}} - \frac{1}{Z_i} - \frac{1}{Z_S}} \quad \text{Equation 2}$$

where $Z_{4P}$ is the first impedance value, $Z_{2P}$ is the second impedance value, $Z_i$ is the input impedance value of the impedance measuring circuit, and $Z_s$ is the internal impedance of the current source.

6. The method of claim 1, further comprising:

changing an effective value of the internal impedance of the current source by connecting a parallel impedance to the current source.

7. The method of claim 6, wherein the parallel impedance is smaller than the internal impedance of the current source.

* * * * *